(12) United States Patent
DeLaRiva et al.

(10) Patent No.: US 11,745,169 B1
(45) Date of Patent: Sep. 5, 2023

(54) SINGLE ATOM METAL DOPED CERIA FOR CO OXIDATION AND HC HYDROGENATION/OXIDATION

(71) Applicants: Andrew DeLaRiva, Albuquerque, NM (US); Abhaya Krishna Datye, Albuquerque, NM (US); Christopher Ryan Riley, Albuquerque, NM (US)

(72) Inventors: Andrew DeLaRiva, Albuquerque, NM (US); Abhaya Krishna Datye, Albuquerque, NM (US); Christopher Ryan Riley, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 15/929,719

(22) Filed: May 18, 2020

Related U.S. Application Data

(60) Provisional application No. 62/849,197, filed on May 17, 2019.

(51) Int. Cl.

| | | |
|---|---|---|
| *B01J 21/02* | (2006.01) | |
| *B01J 21/06* | (2006.01) | |
| *B01J 21/10* | (2006.01) | |
| *B01J 23/10* | (2006.01) | |
| *B01J 23/42* | (2006.01) | |
| *B01J 23/63* | (2006.01) | |
| *B01J 23/72* | (2006.01) | |
| *B01J 23/745* | (2006.01) | |
| *B01J 23/75* | (2006.01) | |

(Continued)

(52) U.S. Cl.
CPC ............... *B01J 23/83* (2013.01); *B01J 21/10* (2013.01); *B01J 23/42* (2013.01); *B01J 35/1014* (2013.01); *B01J 35/1019* (2013.01); *B01J 37/0201* (2013.01); *B01J 37/036* (2013.01); *B01J 37/04* (2013.01); *B01J 37/088* (2013.01); *C07C 5/03* (2013.01); *C07C 5/09* (2013.01); *B01D 53/94* (2013.01); *B01D 2255/1021* (2013.01); *B01D 2255/20753* (2013.01); *B01D 2255/9207* (2013.01); *C07C 2521/04* (2013.01); *C07C 2521/10* (2013.01); *C07C 2523/42* (2013.01); *C07C 2523/755* (2013.01); *C07C 2523/83* (2013.01)

(58) Field of Classification Search
CPC .... B01J 23/42; B01J 35/1014; B01J 37/0201; B01J 37/036; B01J 37/04; B01J 21/02; B01J 23/10; B01J 23/63; B01J 23/72; B01J 23/745; B01J 23/755; B01J 23/83; B01J 23/8892; B01J 23/8906; B01J 23/8912; B01J 23/8926; B01J 23/894; B01J 21/10; B01J 35/1019; B01J 37/088; B01J 21/066; B01J 23/8986; C07C 5/03
See application file for complete search history.

(56) References Cited

U.S. PATENT DOCUMENTS

| | | | | |
|---|---|---|---|---|
| 4,708,946 A | * | 11/1987 | Ohata .................. | B01D 53/945 502/304 |
| 5,837,642 A | * | 11/1998 | Tanaka ................. | C01G 25/006 502/304 |

(Continued)

*Primary Examiner* — Cam N. Nguyen
(74) *Attorney, Agent, or Firm* — Gonzales Patent Services; Ellen M. Gonzales

(57) ABSTRACT

Novel doped oxide and mixed-oxide materials having a metal homogenously dispersed in the form of isolated metal ions throughout the oxide lattice and methods for making the same.

14 Claims, 20 Drawing Sheets

(51) Int. Cl.
*B01J 23/83* (2006.01)
*B01J 23/88* (2006.01)
*B01J 23/89* (2006.01)
*B01J 35/10* (2006.01)
*B01J 37/02* (2006.01)
*B01J 37/03* (2006.01)
*B01J 37/04* (2006.01)
*B01J 37/08* (2006.01)
*C07C 5/03* (2006.01)
*C07C 5/09* (2006.01)
*B01D 53/94* (2006.01)

(56) References Cited

U.S. PATENT DOCUMENTS

| | | | |
|---|---|---|---|
| 6,013,313 A | 1/2000 | Noonan | |
| 6,150,299 A * | 11/2000 | Umemoto | B01J 27/053 423/247 |
| 6,180,075 B1 * | 1/2001 | Lindner | B01J 23/63 423/213.2 |
| 6,214,306 B1 * | 4/2001 | Aubert | C01G 25/00 423/213.2 |
| 6,326,329 B1 * | 12/2001 | Nunan | B01J 23/38 502/242 |
| 6,338,831 B1 * | 1/2002 | Strehlau | B01J 20/041 423/244.07 |
| 6,419,820 B1 * | 7/2002 | Bogdan | B01J 23/626 208/134 |
| 6,492,298 B1 * | 12/2002 | Sobukawa | B01D 53/8628 423/213.5 |
| 6,596,249 B2 * | 7/2003 | Lin | C10G 11/04 423/247 |
| 6,703,343 B2 * | 3/2004 | Park | B01D 53/9422 502/320 |
| 6,706,660 B2 * | 3/2004 | Park | B01D 53/9422 502/241 |
| 6,809,061 B2 * | 10/2004 | Bogdan | B01J 23/626 502/227 |
| 7,166,263 B2 * | 1/2007 | Vanderspurt | C01F 17/241 502/302 |
| 7,582,222 B2 * | 9/2009 | Punnoose | C01G 19/00 252/520.1 |
| 7,838,460 B2 * | 11/2010 | Shimazu | C01B 3/40 423/326 |
| 7,863,217 B2 * | 1/2011 | Minoshima | B01J 35/04 502/325 |
| 8,017,097 B1 * | 9/2011 | Southward | B01J 37/0036 502/305 |
| 8,524,178 B2 * | 9/2013 | Manoharan | C01F 17/34 423/122 |
| 8,709,678 B2 * | 4/2014 | Seo | H01M 8/1253 429/496 |
| 9,314,771 B2 * | 4/2016 | D'Souza | B01J 21/16 |
| 9,393,551 B2 * | 7/2016 | Suzuki | C10K 3/023 |
| 10,017,385 B2 * | 7/2018 | Lee | C01B 3/326 |
| 10,875,011 B2 * | 12/2020 | Gopinath | B01J 37/031 |
| 11,110,396 B2 * | 9/2021 | Minami | B01J 35/023 |
| 2003/0118960 A1 * | 6/2003 | Balmer-Millar | B01J 23/08 431/146 |
| 2004/0004024 A1 * | 1/2004 | Lin | B01J 37/0205 208/120.15 |
| 2009/0105511 A1 * | 4/2009 | Okada | C07C 5/367 585/434 |
| 2009/0170695 A1 * | 7/2009 | Lee | C01B 3/16 502/304 |
| 2009/0280978 A1 * | 11/2009 | Nakamura | B01J 23/894 502/303 |
| 2010/0064771 A1 * | 3/2010 | Punnoose | G01N 33/0027 73/31.05 |
| 2010/0196217 A1 * | 8/2010 | Southward | F01N 3/035 422/168 |
| 2012/0178619 A1 * | 7/2012 | Ji | B01J 35/1019 502/339 |
| 2016/0296915 A1 * | 10/2016 | Nagata | B01J 35/1014 |
| 2016/0318005 A1 * | 11/2016 | Nakahara | B01J 23/8946 |
| 2017/0232424 A1 * | 8/2017 | Furui | B01J 37/0207 502/304 |
| 2019/0126252 A1 * | 5/2019 | Nie | B01J 35/1014 |
| 2020/0123018 A1 * | 4/2020 | Jaroniec | B01J 35/002 |

* cited by examiner

Pt-CeO$_2$

Pt-CeO$_{0.9}$Ni$_{0.1}$O$_2$

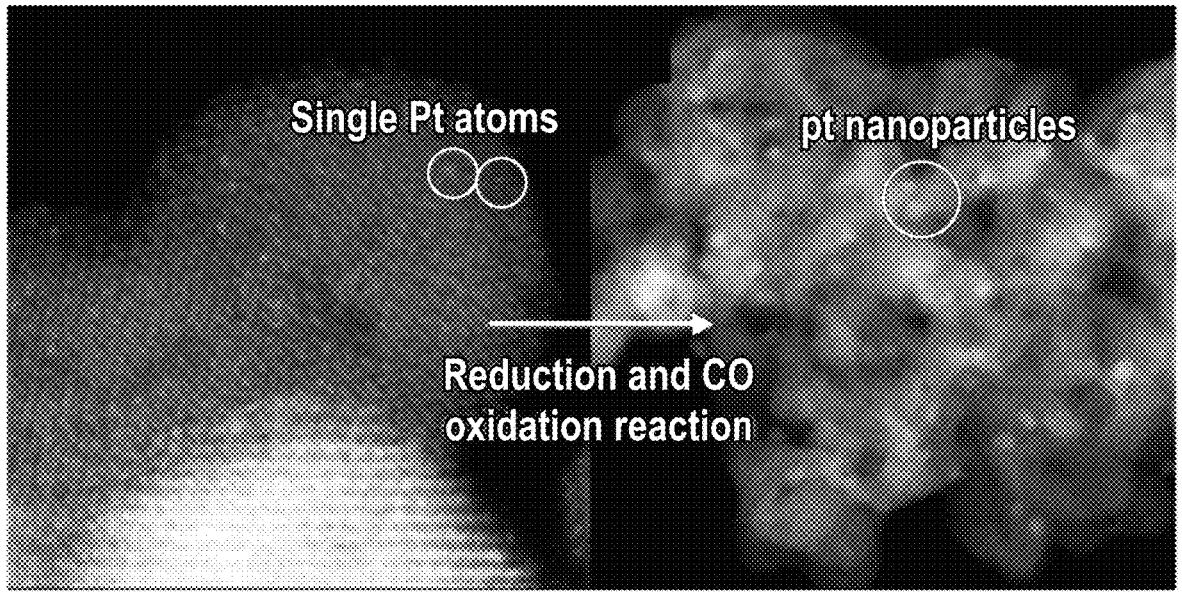
├──┤1nm            ├──┤1nm
FIG. 21         FIG. 22
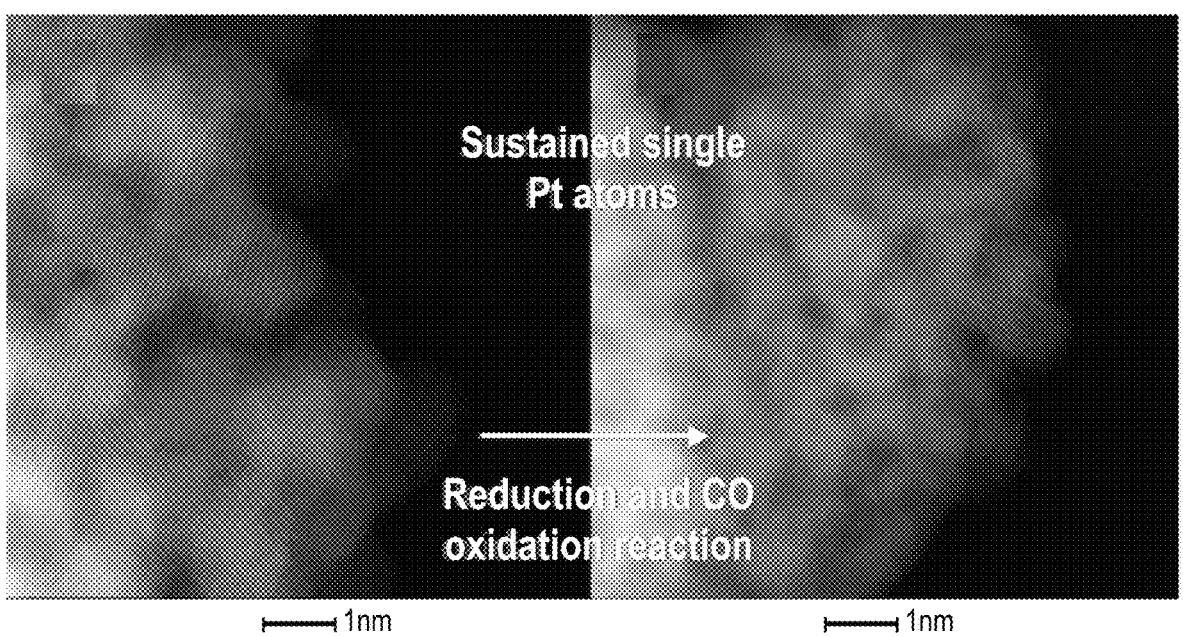
├──┤1nm            ├──┤1nm
FIG. 23         FIG. 24

US 11,745,169 B1

SINGLE ATOM METAL DOPED CERIA FOR CO OXIDATION AND HC HYDROGENATION/OXIDATION

CROSS-REFERENCE TO RELATED APPLICATIONS

The following application claims benefit of U.S. Provisional Application No. 62/849,197, filed May 17, 2019, which is hereby incorporated by reference in its entirety.

STATEMENT REGARDING GOVERNMENT SPONSORED RESEARCH

This invention was made with Government support under Grant No. DE-FG02-05ER15712 awarded by the US Department of Energy. The U.S. Government has certain rights in this invention.

BACKGROUND

Novel materials with useful properties and methods for making the same are greatly desired for a variety of applications. In particular, materials which are useful as catalysts or in catalytic reactions are greatly desired as the world searches for novel and affordable methods for energy production, materials production, and elimination of greenhouse gasses and other undesirable or harmful environmental pollutants. Palladium catalysts are the most commonly used and understood but are very expensive and may not be ideal for all desirable reactions. For example, when traditional palladium catalysts are used in the alkyne hydrogenation reactions that are commonly used in the plastics industry, the palladium catalysts tend to over hydrogenate ethylene to ethane and oligomerize the corresponding products, resulting in undesired products. A common method for addressing this approach involves alloying palladium with other metals, which has raised additional issues—as the metals incorporated into the catalyst (gold, silver, gallium) are expensive and the bimetallic catalysts often phase separate under reaction conditions or during regeneration.

Accordingly, novel materials that are affordable and useful for applications including, but not necessarily limited to catalysis of a variety of reactions are greatly desired.

Moreover, many of the synthesis methods for commonly used catalysts involve the production of undesirable or even harmful by-products and/or complicated, difficult, or even potentially dangerous materials and protocols. Accordingly, novel materials that are synthesized using simple and safe processes that use safe materials, produce no harmful by-products and result in little to no waste are also greatly desired.

SUMMARY

The present disclosure provides novel doped oxide and mixed-oxide materials and methods for making the same. According to an embodiment, the present disclosure provides a metal-doped oxide material such as a ceria, spinel, or perovskite and methods for making the same. According to various embodiments the metal-doped oxide material has novel and in some cases unexpected qualities. According to a specific embodiment, the oxide material is doped with one or more metals. According a specific embodiment, the oxide material is doped with one or more ionic metals. According to an even more specific embodiment, the oxide material has a high surface area and is doped with uniform distribution of one or more ionic or non-ionic metals.

BRIEF DESCRIPTION OF THE DRAWINGS

FIG. 21 is an image of 1 wt % platinum on standard ceria oxide in its as-prepared state.

FIG. 22 is an image of 1 wt % platinum on standard ceria oxide after reduction showing the formation of Pt nanoparticles.

FIG. 23 is an image of 1 wt % platinum on SG $Ce_{0.9}Ni_{0.1}O_{2-\delta}$ material of the present disclosure in its as-prepared state.

FIG. 24 is an image of 1 wt % platinum on SG $Ce_{0.9}Ni_{0.1}O_{2-\delta}$ material of the present disclosure after reduction showing the absence of any Pt nanoparticles.

DETAILED DESCRIPTION

Figure 1:
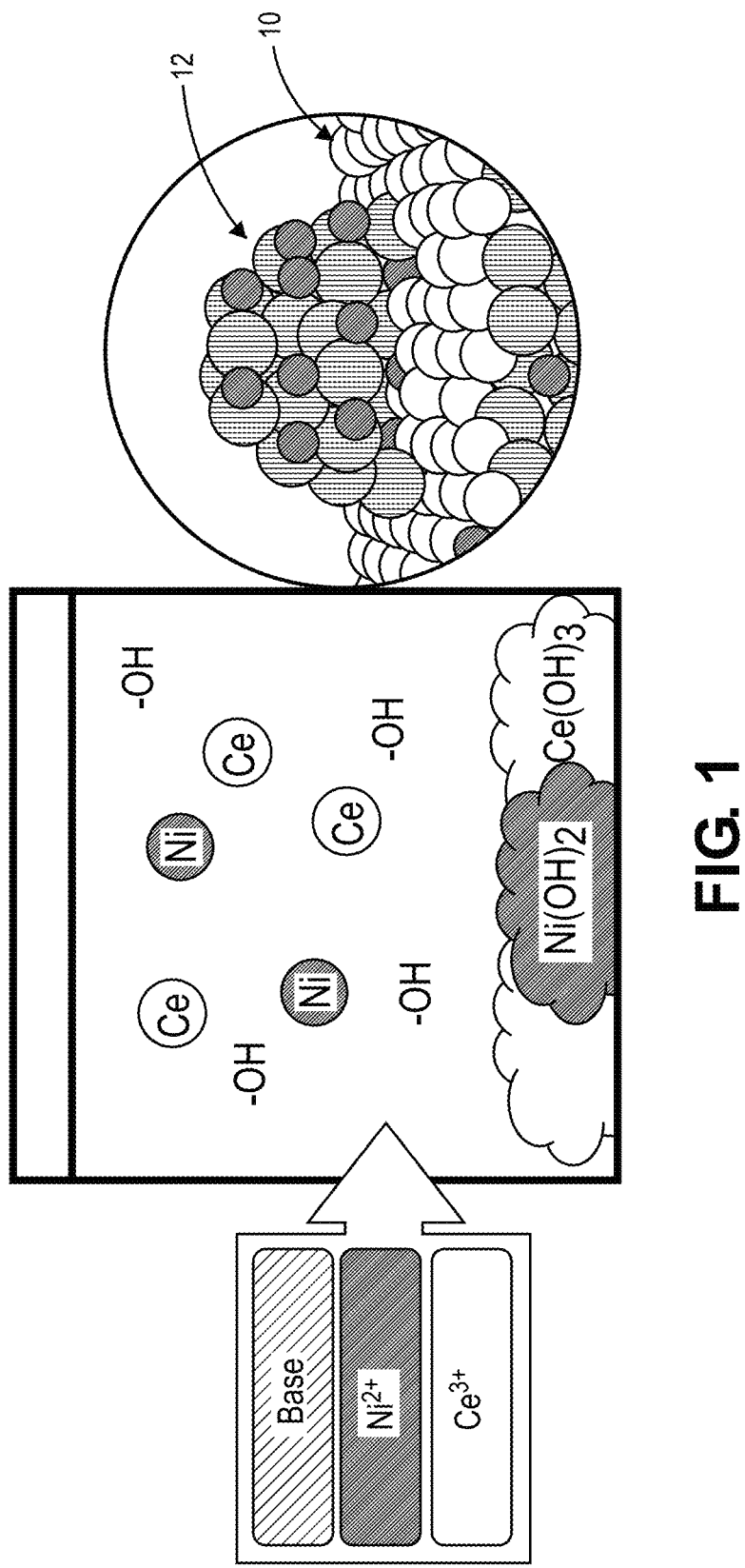
FIG. 1 is a schematic illustration of a specific embodiment of a coprecipitation process for forming metal ceria materials using $Ni^{2+}$ as the metal.

According to various embodiments the present disclosure provides novel materials and methods for making the same. According to an embodiment, the materials are useful for a variety of applications including, but not limited to, catalysis of selective alkyne hydrogenation, alkene hydrogenation, as an oxygen transfer agent, use in catalytic converters to reduce carbon monoxide emissions, dry reforming of methane, etc.

According to a first embodiment, the present disclosure provides a novel doped oxide and mixed-oxide materials and methods for making the same. For ease of reference, the materials described herein may be interchangeably referred to as oxide materials or supports, though it should be clear from the disclosure that the "oxide supports" of the present disclosure are useful for a variety of applications not limited solely to supports for other materials. In general, the ceria is doped with a metal to produce a material having novel and in some cases unexpected qualities. According to a specific embodiment, the oxide material is doped with one or more metals. According a specific embodiment, the oxide material is doped with one or more ionic metals. According to an even more specific embodiment, the ceria oxide material has a high surface area and is doped with uniform distribution of one or more ionic or non-ionic metals.

For the purposes of the present disclosure, the term "decorated" as in "oxide support 'decorated' with a metal" is intended to mean that the decorated metal presents entirely or primarily on the surface of the parent oxide.

For the purposes of the present disclosure, the term "doped" as in "ceria 'doped' with a metal" is intended to mean the doped metal is uniformly distributed into the parent oxide. For the purposes of the present disclosure, the term "high surface area" in intended to mean a surface area of greater than 120 $m^2/g$. A "moderate surface area" is a surface area of between 60 and 120 $m^2/g$. A "low surface area" is a surface area of less than 60 $m^2/g$.

For the purposes of the present disclosure, the term "homogenous" in reference to the distribution of dopants in the oxide support is intended to mean that the dopant is not segregated to form a separate phase.

According to a specific embodiment, suitable metal dopants include, but are not limited to, transition metals such as nickel, platinum, copper, iron, manganese, aluminum, zirconium, alkaline earth metals, post transition metals, lanthanides and combinations, including mixtures thereof. Of course it will be understood that non-metal dopants such as nitrogen, may also be included and are well known in the industry.

One oxide suitable for use with the methods of the present disclosure is ceria. Ceria ($CeO_2$) is an oxide of the rare earth metal cerium. According to various embodiments, decorated or doped ceria can be formed using a variety of techniques, each of which, as described below, produce a final material with different surface area and metal distribution. Examples of doping techniques include, for example, wetness impregnation, coprecipitation, solution combustion synthesis, and sol-gel synthesis. (See, e.g., Riley et al., "Synthesis of Nickel-Doped Ceria Catalysts for Selective Acetylene Hydrogenation" ChemCatChem 2019, 11, 1526-1533, which is hereby incorporated by reference for all purposes.) For example, ceria can be doped with a metal using a wetness impregnation (WI) technique. In general a WI metal-ceria sample is synthesized by adding a metal nitrate solution dropwise to ceria that has been calcined at 500° C. The resulting material is then dried at 110° C. overnight and then calcined. This technique generally results in the deposited metal presenting primarily on the surface of the ceria, rather than being incorporated into the ceria lattice as a true dopant.

As another example, ceria can be doped with a metal using a coprecipitation (CP) technique. In general, a CP metal-ceria sample is synthesized by adding an appropriate amount of metal and cerium precursor in a solvent such as deionized (DI) water under agitation (e.g., stirring). A base such as KOH can then be added to bring the pH of the resulting solution to 10. A pH of greater than 9 is maintained, for example by continued or repeated addition of a base solution, until a cerium and metal hydroxide precipitate forms. The cerium and metal hydroxide precipitate is then allowed to settle. The precipitate is then collected, washed, dried, and then calcined. This technique generally results in a dopant that is integrated into a ceria lattice having moderate surface area. FIG. 1 is a schematic illustration of a specific embodiment of this process using $Ni^{2+}$ as the metal. As shown, the final product results in a ceria substrate 10 integrated with Ni segregated as NiO 12.

As yet another example, ceria can be doped with metal using solution combustion synthesis (SCS) technique. In general, an SCS metal-ceria sample is synthesized by adding ammonium cerium (IV) nitrate, metal nitrate hexahydrate, and urea to a solvent such as DI water. The mixture is then agitated (i.e. by stirring) and heated to evaporate excess solvent and produce a gel. The gel is then combusted in a furnace. Following combustion, the sample can be ground and calcined. This technique generally results in an agglomerated dopant integrated into a ceria lattice having low surface area.

As still another example, ceria can be doped with metal using a sol-gel (SG) technique. In general, a SG metal-ceria sample is synthesized by dissolving a polymer in a solvent such as DI water. The polymer may be dissolved, for example, by vigorous agitation (stirring) and mild heating. The solution is then cooled and appropriate amounts of metal and cerium nitrates added. The solution is then agitated (or stirred) for a period of time and then dried (for example in a box furnace) until a hard gel is formed. The resulting gel is then turned into a powder (for example by coarsely grinding the gel) and calcined. This technique generally results in a high surface area cerium oxide having a high loading of metal ions in a uniform or homogenous distribution throughout the lattice. Table 1 shows the surface area of various metal-ceria samples formed using the SG technique, where the number 10 refers to the atom % of the dopant (atoms of dopant per 100 atoms of metal) in the doped sample.

TABLE 1

| Sample | Specific surface area (m²/g) |
| --- | --- |
| $CeO_2$ | 165 |
| PVP-10-Ni | 170 |
| PVP-10-Cu | 179 |
| PVP-10-Fe | 150 |
| PVP-10-Mn | 179 |

Figure 2:
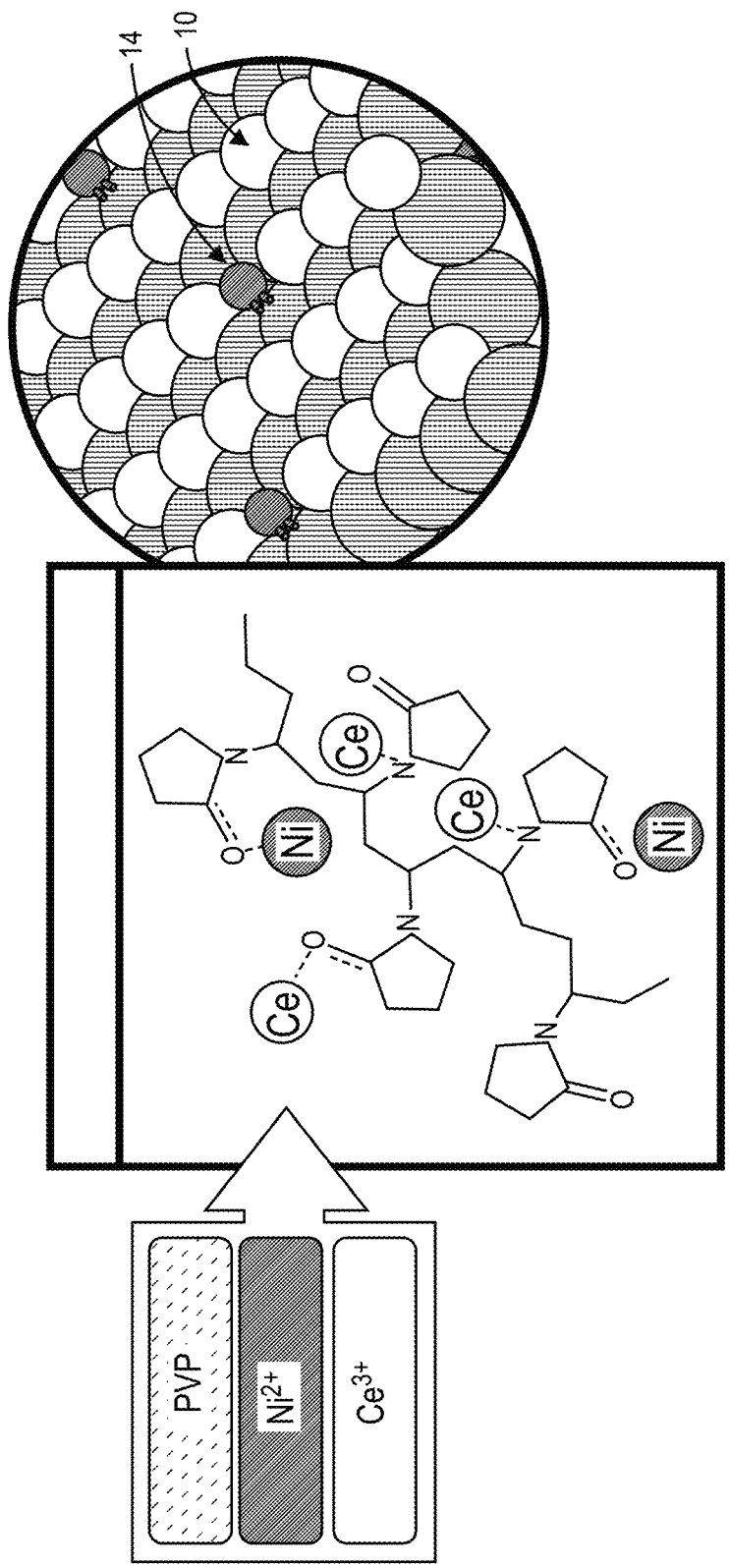
FIG. 2 is a schematic illustration of a specific embodiment of a sol-gel based process for forming metal ceria materials using $Ni^{2+}$ as the metal.

This combination of high surface area and uniform distribution was not achieved using any of the other methods and, as described in greater detail below, produced a material having unique physical properties and that was not only highly selective for alkyne hydrogenation, but also highly active as an oxygen transfer agent, making it particularly useful for a wide variety of applications. FIG. 2 is a schematic illustration of a specific embodiment of this process using $Ni^{2+}$ as the metal. As shown the final product results in a ceria substrate 10 integrated with isolated Ni ion dopants 14. The fact that the SG process results in the presence of isolated metal ion dopants is important as it appears to increase the resulting material's ability to act as a catalyst and a catalyst support.

In general, the polymer used in the SG technique should have functional groups that attract positive ions. An exemplary polymer for use in SG technique is polyvinylpyrrolidone (PVP) which is commonly used in many biological and non-biological applications. Other possible polymers include polyethylene glycol (PEG) and hydroxypropyl cellulose (HPC).

As stated above, the SG technique generally results in a final material having a high surface area. However, it will be appreciated that the actual surface area of the final material can be tailored based on the concentration of polymer used with increased amounts of polymer resulting in increased surface area. For example, experiments varying the amounts of PVP in $Ce_{0.8}Ni_{0.2}O_{2-\delta}$ a samples produced the following results:

TABLE 2

| Mass of PVP used (g) | Specific surface area (m²/g) |
| --- | --- |
| 1 | 76 |
| 2.5 | 121 |
| 5.0 | 147 |
| 7.5 | 152 |

Alternatively or additionally, the surface area of the final material can be tailored based on the heating rate during the calcination step. For example, experiments varying the heating rate produced the following results:

TABLE 3

| Heating rate (° C./min) | Specific surface area (m²/g) |
| --- | --- |
| 1 | 159 |
| 10 | 148 |
| Furnace preheated to 500° C. | 96 |

As stated above, the material produced using the SG technique has unique physical characteristics that are not seen in metal doped oxide materials formed using other techniques. As discussed, the SG technique produces a high surface area material (assuming a sufficient amount of polymer and heating rate are used, as described above.) However, the material is also unique in the homogeneity (i.e. uniform metal ion distribution) of the resulting structure as measured via energy dispersive spectroscopy (EDS) in a TEM and in an SEM.

Advantages of the SG doped oxide catalyst described herein include that unlike many commonly used catalysts, the SG doped oxide catalyst can be exposed to air, is stable over multiple uses, and does not require activation. For example, the problem with standard nickel catalysts is that NiO is not active and must be reduced to Ni at high temperatures, but then they cannot be exposed to air, unless they are passivated very carefully. In contrast, the presently described oxide catalysts are active as prepared and can be exposed to air, leading to significant ease of use in comparison.

Moreover, the unique physical properties of the SG doped ceria make the material useful for a wide variety of applications. For example, as described in greater detail in the Examples section, the presently described SG doped ceria demonstrates excellent catalytic activity, is selective for alkyne hydrogenation, and is highly suitable for catalytic converter applications.

Moreover, the SG doped ceria described herein can be used as a support for other catalytic materials including, but not limited to platinum. For example, experimental data described in the Examples section below shows that platinum supported on Ni-doped ceria formed using the SG technique remains atomically dispersed and has stable performance.

Furthermore, as stated above, the present disclosure contemplates materials that are doped with multiple metals. As demonstrated in the Examples section below, such multi-metal doped ceria materials may provide advantages over single metal doped ceria materials. For example, it was found that copper+zirconium and copper+aluminum co-doped SG ceria had improved hydrothermal stability and reactivity compared with copper-doped SG ceria.

While many of the examples and much of the description herein is directed towards ceria oxide materials, it should be understood that the present disclosure contemplates other suitable oxide (and mixed-oxide) supports made using the techniques described herein including, for example, spinels, perovskites, and the like.

For example, the SG technique described herein was used to produce pure (as seen by both XRD and TEM) $MgAl_2O_4$ spinels by mixing Mg and Al nitrates in desired proportions with the dissolved polymer, as described above. The resulting $MgAl_2O_4$ contained small crystallites (5-8 nm), had relatively high surface area (up to 130 m²/g), and had no detectable MgO, $Al_2O_3$ or amorphous surface phases.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

Riley et al., Design of Effective Catalysts for Selective Alkyne Hydrogenation by Doping of Ceria with a Single-Atom Promotor J. Am. Chem Soc. (2018), https://doi.org/10.1021/jacs.8b07789_jacs.8b07789

C. Riley, A. De La Riva, S. Zhou, Q. Wan, E. Peterson, K. Artyushkova, M. Farahani, H. Friedrich, S. Lin, H. Guo, L. Burkemper, N.-V. Atudorei, A. Datye, Synthesis of nickel-doped Ceria catalysts for selective acetylene hydrogenation, ChemCatChem. 11 (2019) 1526-1533, https://doi.org/10.1002/eete.201801976.

C. Riley, G. Canning, A. De La Riva, S. Zhou, E. Peterson, A. Boubnov, A. Hoffman, M. Tran, S. Bare, S. Lin, H. Guo, Environmentally benign synthesis of a PGM-free catalyst for low temperature CO oxidation. App Cat B. 264 (2020), https://doi.org/10.1016/j.apcatb.2019.118547

EXAMPLES

Synthesis of 1.5 wt % Ni—$CeO_2$ Samples Via Wet Impregnation (WI)

Nickel nitrate solution was added dropwise to ceria that had been calcined at 500° C. The resulting material was dried at 110° C. overnight and then calcined at 500° C. for 2 hours.

Synthesis of 1.5 wt % Ni—$CeO_2$ Samples Via Coprecipitation (CP)

3.1 g cerium (III) nitrate hexahydrate and 0.093 g nickel (II) nitrate hexahydrate precursors were dissolved in 100 ml DI water while stirring. A 1 M solution of potassium hydroxide was prepared. KOH solution was then added dropwise to bring the pH to 10. Additional KOH was added over the next hour to maintain pH>9. Stirring was then stopped to allow cerium and nickel hydroxide precipitate to settle overnight. The precipitate was then repeatedly washed with DI water. The resulting precipitate was dried at 110° C. overnight and then calcined at 500° C. for 2 hours.

Synthesis of 1.5 wt % Ni—$CeO_2$ Samples Via Solution Combustion Synthesis (SCS)

5 g of ammonia cerium (IV) (ACS reagent>98.5%) nitrate, 0.118 g of nickel (II) nitrate hexahydrate, and 2.231 g urea (high purity) were added to DI water. The mixture was stirred and heated for approximately half an hour to evaporate excess water. The resulting gel was placed into a furnace at 400° C. to combust. Following combustion, the sample was ground and calcined at 400° C. for 4 hours.

Synthesis of 1.5 wt % Ni—$CeO_2$ Samples Via Sol-Gel Synthesis (SG)

5 g of polyvinylpyrrolidone (40,000 average molecular weight) was dissolved in 100 ml of DI water under vigorous stirring and mild heating. The solution was cooled and 3.1 g of cerium (III) nitrate hexahydrate and 0.093 g of nickel (II) nitrate hexahydrate were added. The solution was stirred for 1 hour and then dried at 110° C. in a box furnace to form a hard gel. The resulting gel was coarsely ground and calcined at 500° C. for 2 hours with ramp rate of 1° C./min.

Characterization of Ni—$CeO_2$ Samples

Table 4 shows the EPMA, BET and XRD results for the CP, SG, and SCS samples as well as a control $CeO_2$ sample. XRD analysis demonstrated that the lattice parameter of the wet impregnated sample is near that of unmodified $CeO_2$, which suggests that Ni within this sample does not incorporate as dopant, but is instead, deposited on the surface of the material.

TABLE 4

| Sample | Nickel Composition [wt %] | Specific Surface Area [m²/g] | $CeO_2$ crystal size [nm] | $CeO_2$ lattice parameter [Å] |
| --- | --- | --- | --- | --- |
| $CeO_2$ | — | 87.7 | 8.1 | 5.4127 |
| 1.5-CP | 1.54 | 81.4 | 5.0 | 5.4096 |
| 1.5-SG | 1.42 | 147.7 | 7.4 | 5.4060 |
| 1.5-SCS | 1.48 | 44.0 | 7.7 | 5.4090 |

Interestingly, XRD analysis showed that materials formed using the SG technique, even at high nickel loading (8 wt %), produced no crystalline NiO phase, resulting in ionic nickel homogenously dispersed throughout the ceria lattice.

Figure 3:
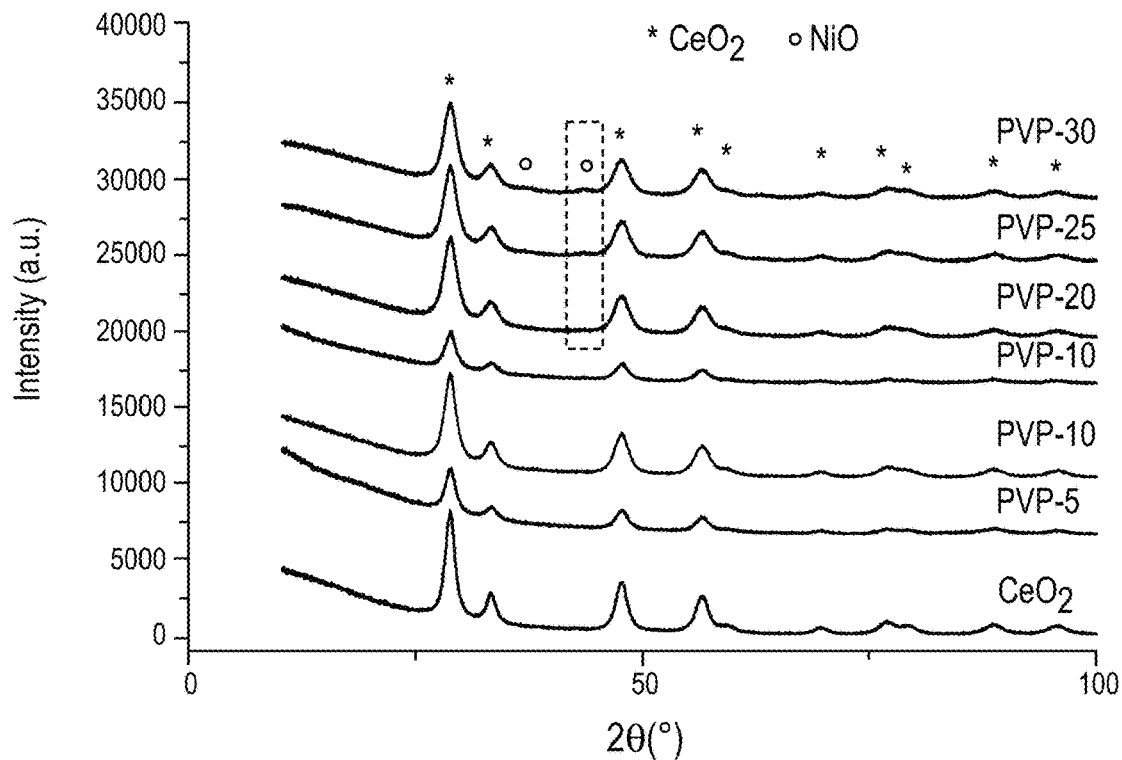
FIG. 3 shows XRD patterns for Ni-doped ceria samples using the sol-gel method of the present disclosure using various amounts of nickel dopant.
Figure 4:
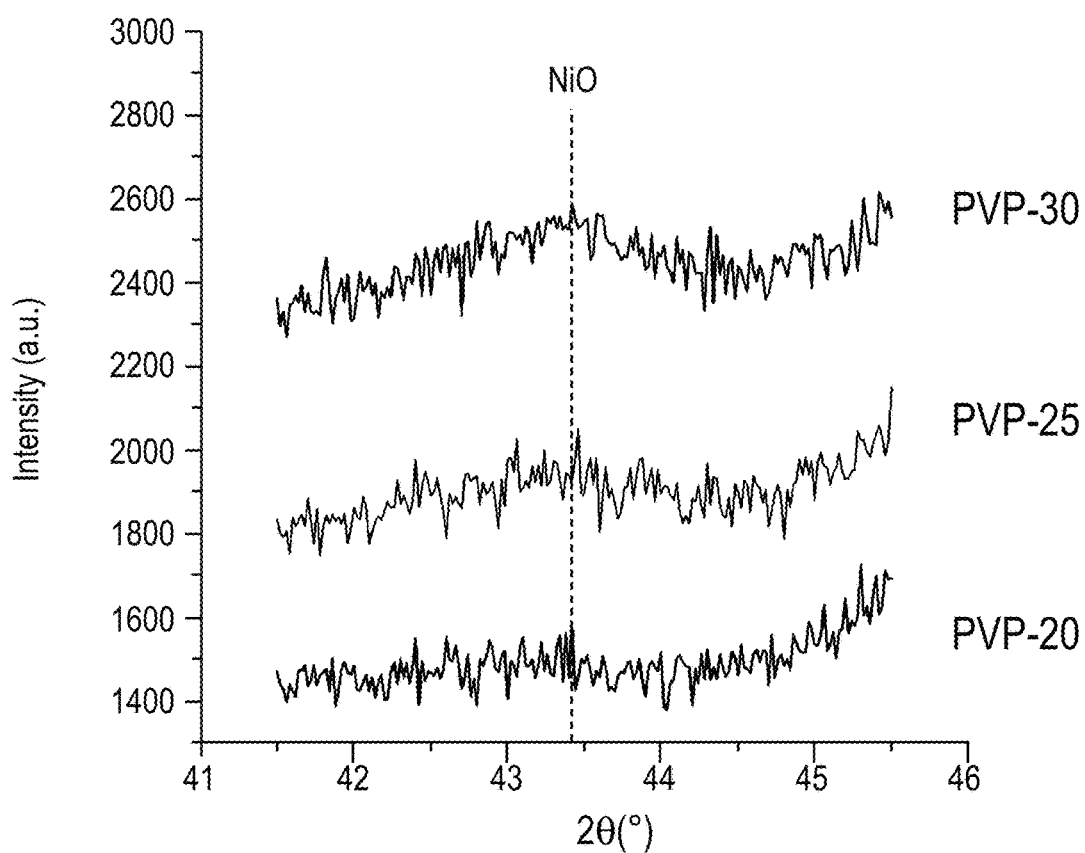
FIG. 4 shows an expanded XRD pattern of Ni-doped ceria samples using the sol-gel method of the present disclosure using various amounts of nickel dopant.

FIGS. 3 and 4 show SG Ni-doped ceria samples made with varying amounts of Nickel dopant. In the figure, the number after the hyphen shows the atomic percent of nickel dopant (ex. PVP 10 has the formula $Ce_{0.9}Ni_{0.1}O_{2-\delta}$). Nickel oxide peaks don't appear until 25 atomic percent nickel dopant is used. The SG method enables the incorporation of 20 atomic percent dopant into ceria, which is very high compared to other synthesis techniques. This figure, along with Table 4 show that nickel is incorporated into ceria, as opposed to segregating as NiO phase. Furthermore, the shrinking of $CeO_2$ lattice parameter, shown in Table 4, demonstrates that nickel is effectively incorporated into the ceria crystal structure.

Figure 5:
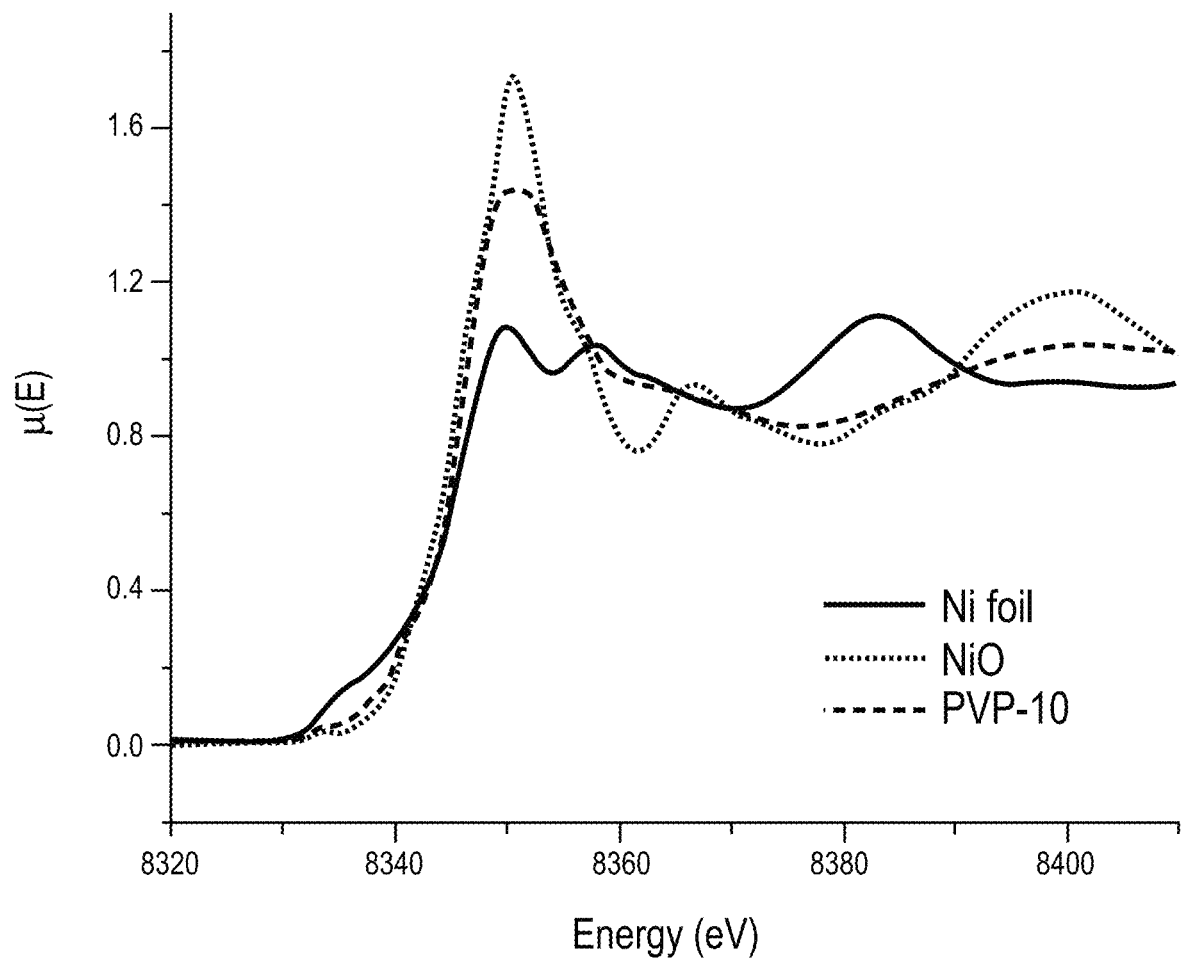
FIG. 5 is x-ray absorption near edge structure (XANES) of Ni foil, Ni oxide, and Ni-doped ceria formed using the sol-gel method of the present disclosure.

FIG. 5 are XANES (x-ray adsorption near edge structure) spectra which help to understand the material structure which surrounds nickel in metallic nickel foil, nickel oxide, and SG $Ce_{0.9}Ni_{0.1}O_{2-\delta}$. As shown, nickel in the sol-gel sample has a structure that is very different from that of nickel within NiO or Ni metal. This is further evidence that nickel is indeed incorporated into the ceria structure.

Competitive Acetylene-Ethylene Hydrogenation Performance

Figure 6:
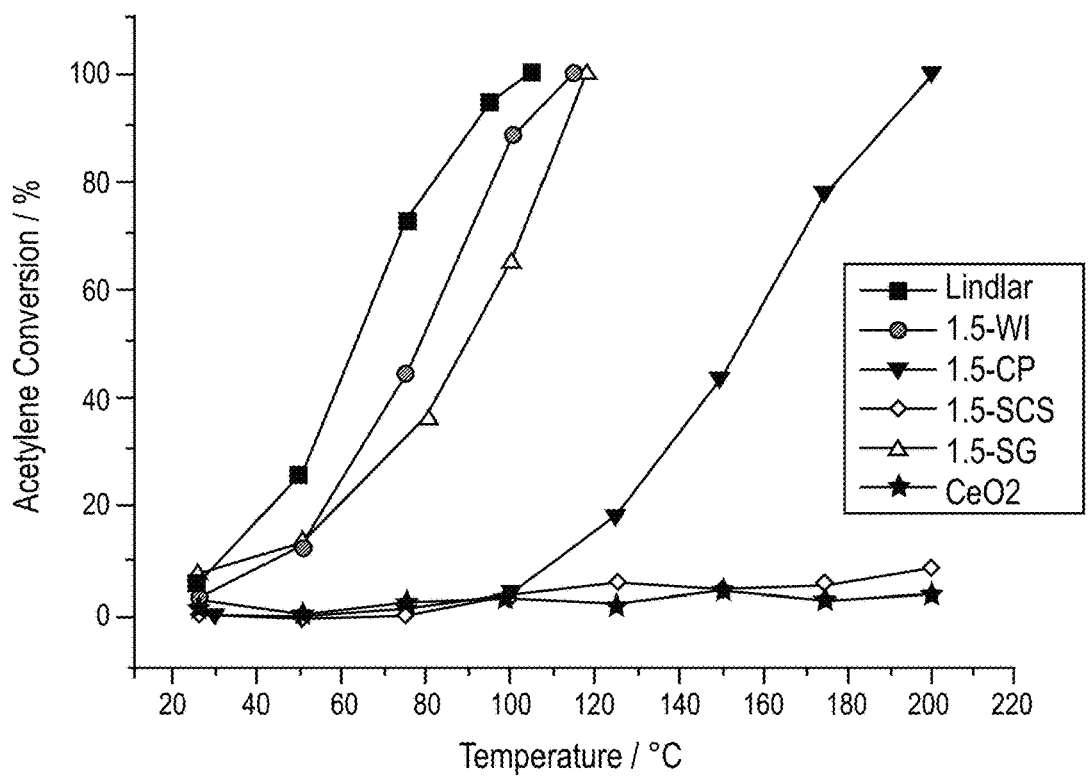
FIG. 6 shows the acetylene hydrogenation performance of various samples as a function of temperature.
Figure 7:
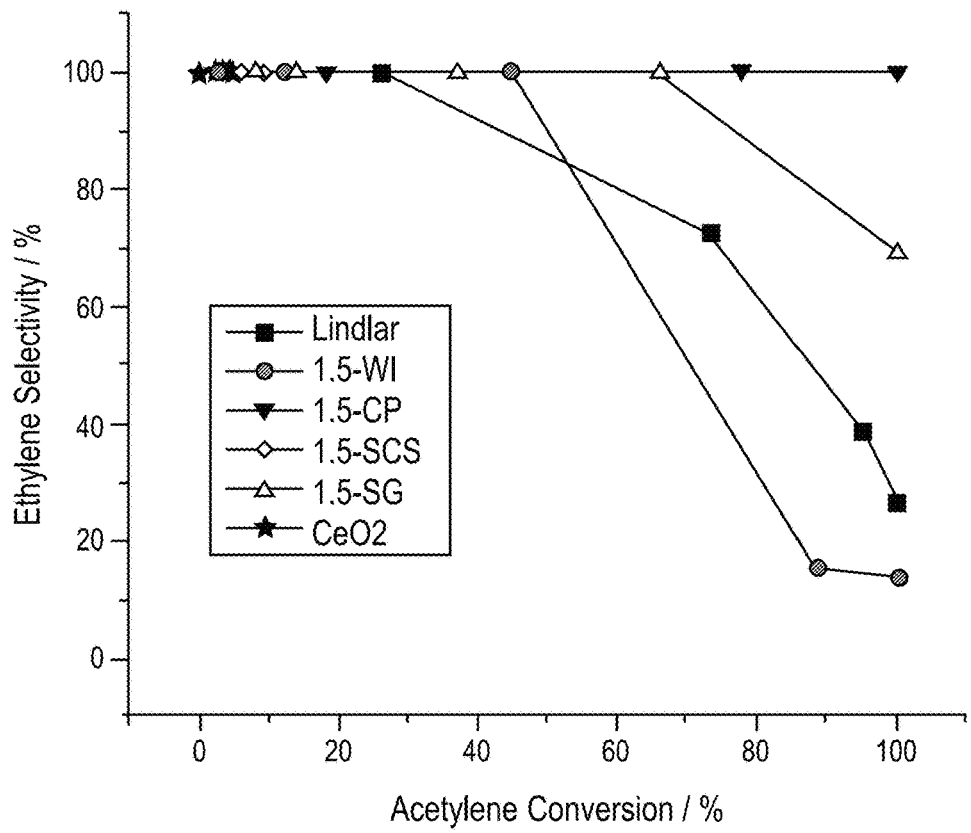
FIG. 7 shows ethylene selectivity of the various samples as a function of acetylene conversion.

FIGS. 6 and 7 shows the competitive hydrogenation performance of 200 mg of each of the Ni—$CeO_2$ samples using a 70:1 mixture of ethylene to acetylene. 30 mg of a Lindlar palladium catalyst and 200 mg of $CeO_2$ were used as a comparisons. While the Lindlar palladium catalyst is more active than the nickel-ceria samples, both the Lindlar and 1.5-WI samples produced large amounts of ethane or oligomers at high acetylene conversions. Remarkably, the 1.5-SG sample did not produce ethane until 100% conversion was achieved. The 1.5CP sample achieved 100% conversion without over-hydrogenating ethylene. While the 1.5-SCS and $CeO_2$ samples also did not produce ethane, their activities were quite low due to the lack of active sites in $CeO_2$ and the low surface area of 1.5-SCS. This example demonstrates ability of the SG sample to perform selective hydrogenation of acetylene in the presence of excess ethylene.

Ethylene Hydrogenation Performance

Figure 8:
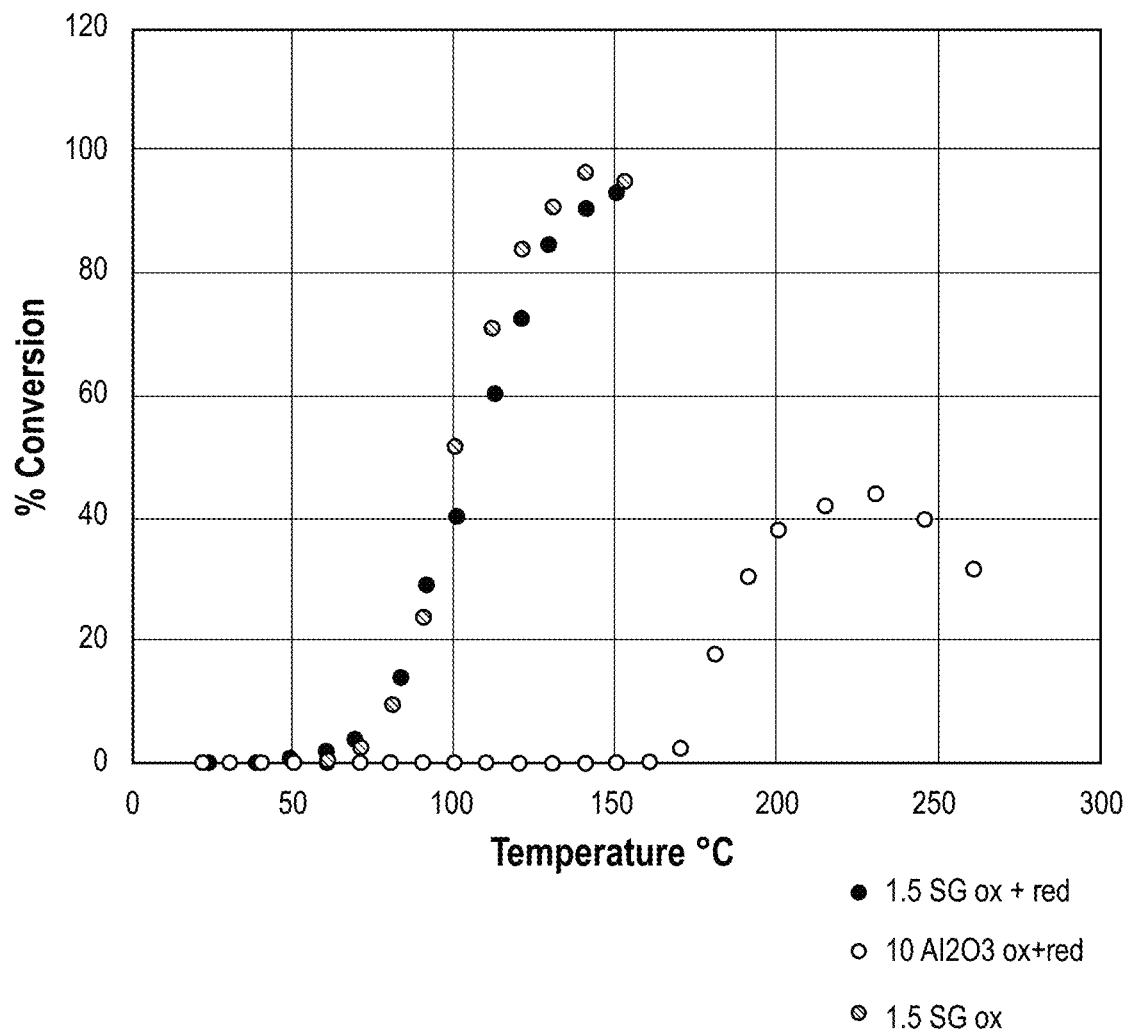
FIG. 8 is a comparison of ethylene hydrogenation activity of a conventional 10 wt % Ni on alumina catalyst and the SG Ni—$CeO_2$ of the present disclosure.
Figure 9:
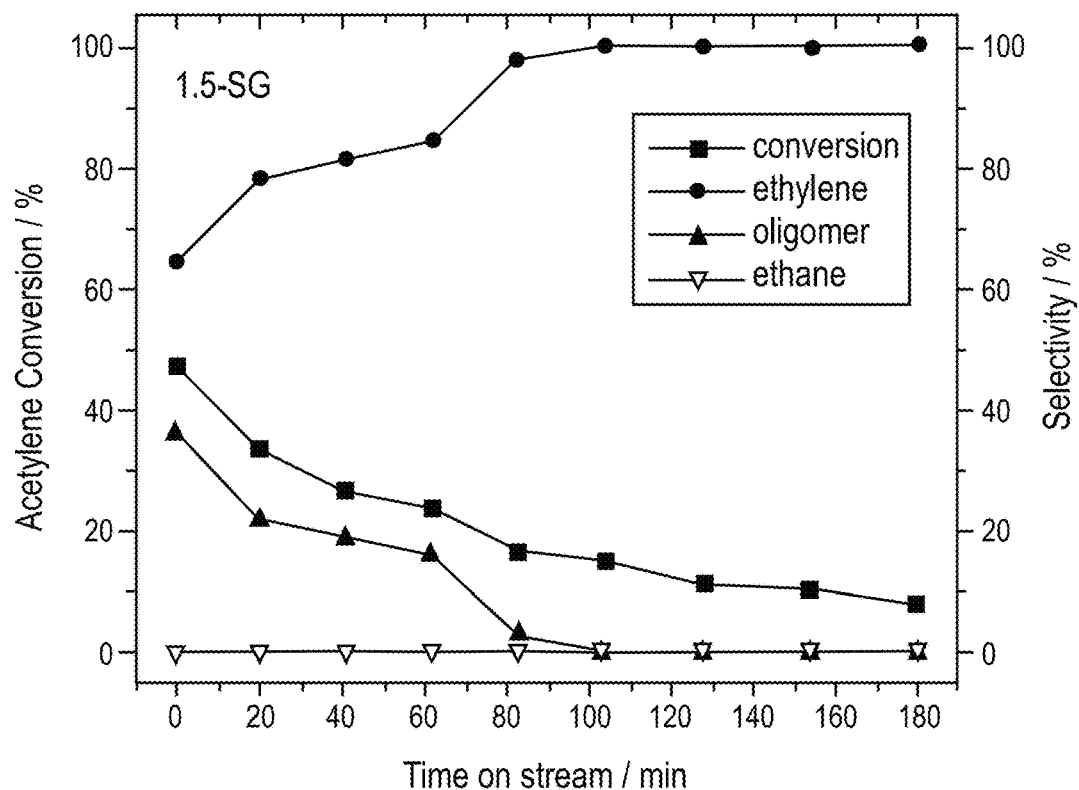
FIG. 9 is the result of isothermal testing using acetylene as the sole hydrocarbon feed gas on 1.5 SG sample.
Figure 10:
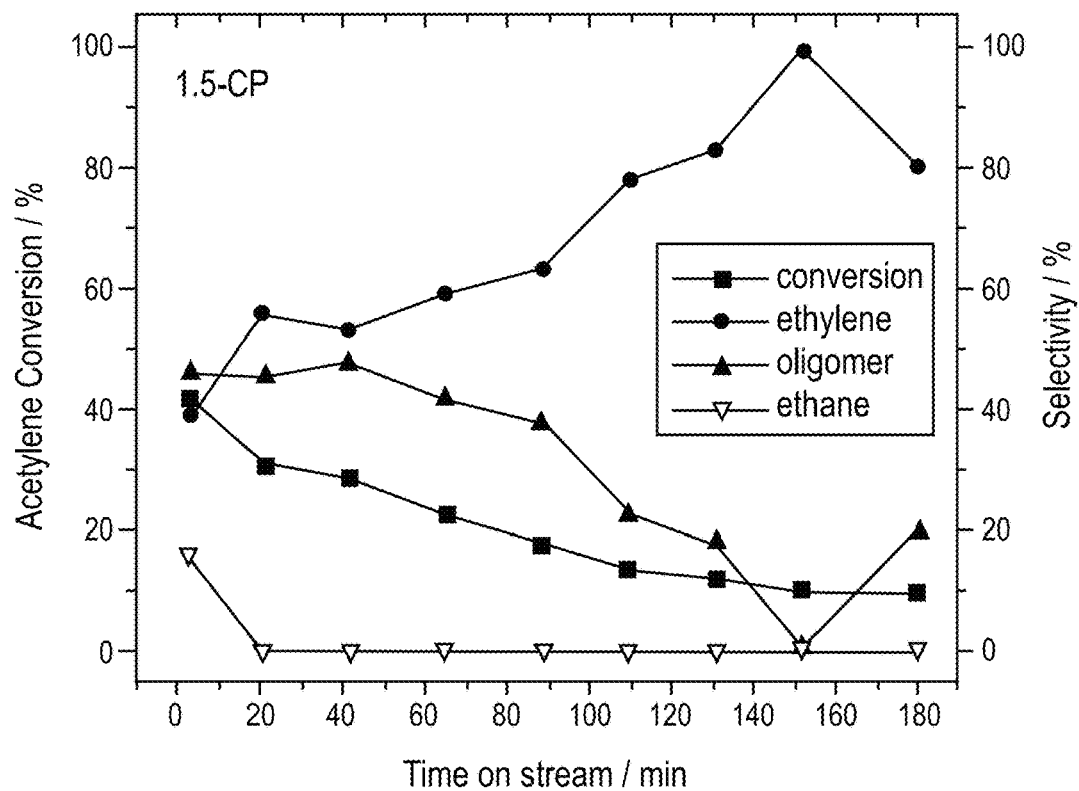
FIG. 10 is the result of isothermal testing using acetylene as the sole hydrocarbon feed gas on 1.5 CP sample.
Figure 11:
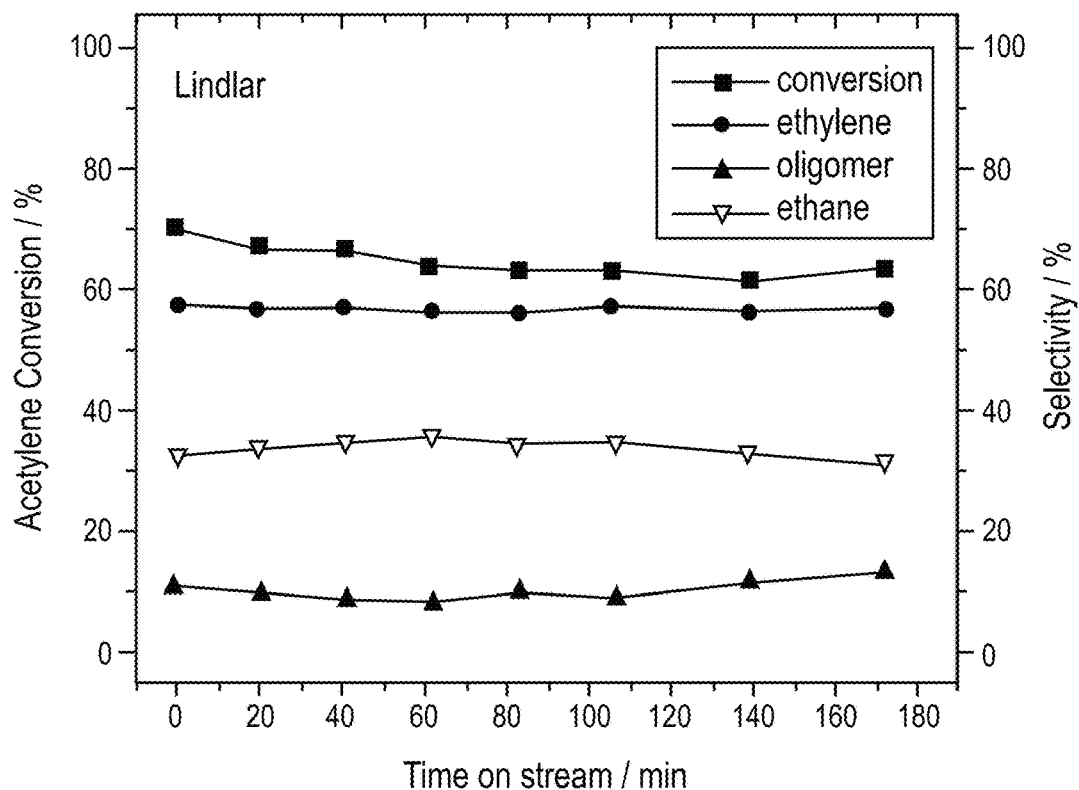
FIG. 11 is the result of isothermal testing using acetylene as the sole hydrocarbon feed gas on Lindlar catalyst sample.
Figure 12:
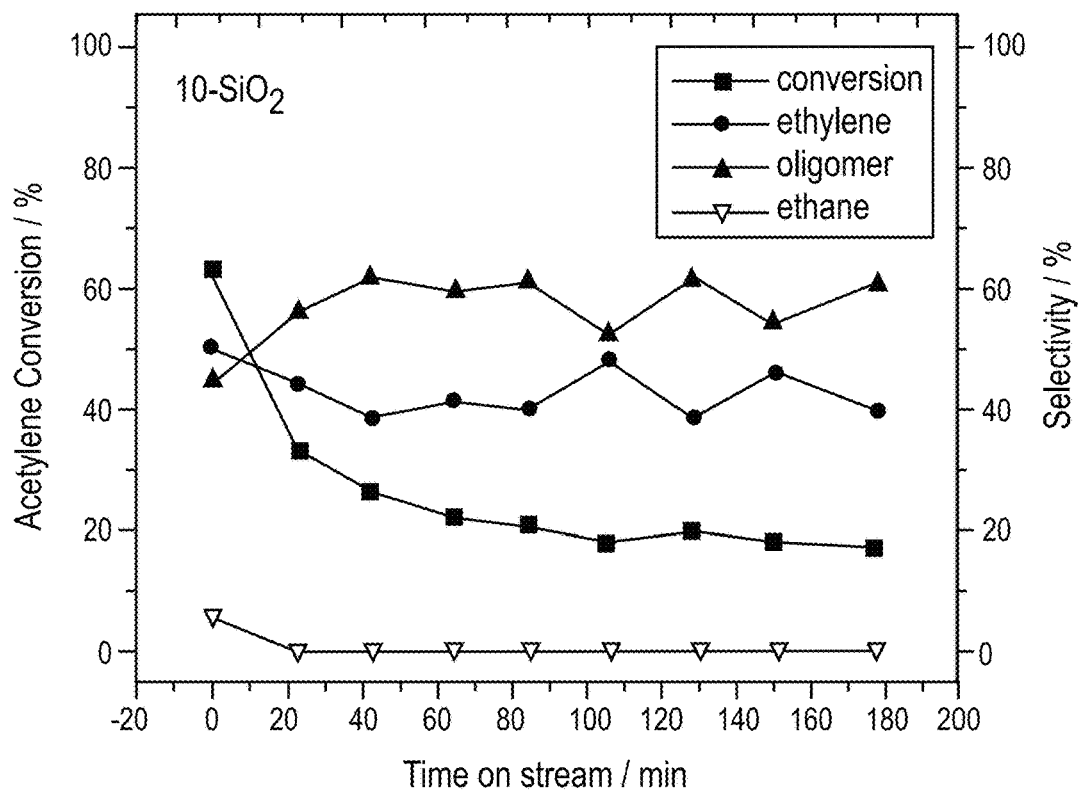
FIG. 12 is the result of isothermal testing using acetylene as the sole hydrocarbon feed gas on 10-$SiO_2$ sample.

FIG. 8 shows a comparison of ethylene hydrogenation activity of a conventional 10 wt % Ni on alumina catalyst and the 1.5 SG Ni—$CeO_2$. For this test, 20 mg of each catalyst was used. The catalyst was subjected first to oxidation in 50 ml/min of flowing air for 1 hr, and then each catalyst was reduced by flowing 2 ml/min of $H_2$ and 48 ml/min of $N_2$ for 1 hour. The reaction was performed with 2 ml/min of ethylene, 23 ml/min of $N_2$ and 25 ml/min of $H_2$. The nickel-doped ceria catalyst has less than one fifth as much nickel as the alumina-supported Ni, but has superior performance compared with the conventional nickel catalyst when both catalysts go through an oxidation and reduction pretreatment step. The performance of the 1.5 SG Ni—$CeO_2$ is similar after just an oxidation treatment, with no reduction step, but the 10% Ni/$Al_2O_3$ shows no activity after oxidation. The reason is that the conventional Ni/$Al_2O_3$ catalyst deactivates when oxidized, by forming NiO. In contrast, the SG doped Ni sample contains ionic Ni, which is not affected by these oxidation-reduction pretreatment steps. Having a catalyst that is stable in air and still performs hydrogenation could be a big benefit, since metallic Ni catalysts as used in industry have to be handled very carefully in air. If not carefully passivated, Ni/alumina is pyrophoric when exposed to air. This example demonstrates that the SG Ni—$CeO_2$ sample contains Ni in a form that is different from NiO or metallic Ni, allowing it be very effective for hydrogenation.

Oligomer Formation

Oligomer formation is known to influence catalyst selectivity and stability. Accordingly, isothermal testing using acetylene as the sole hydrocarbon feed gas was conducted on 1.5-SG (150 mg) (FIG. 9), 1.5-CP (380 mg) (FIG. 10), Lindlar (15 mg) (FIG. 11), and 10-$SiO_2$ (225 mg) (FIG. 12) samples. Conversion and selectivity values were recorded for 3 hours TOS (time on stream). As shown in FIGS. 9-12, the Lindlar sample is the most stable in terms of conversion and product selectivity. However, ethylene selectivity remained below 60% with ethane selectivity near 30% and oligomer selectivity near 10%. 10-$SiO_2$ (10 wt % Ni/$SiO_2$), which contained nickel nanoparticles (confirmed through XRD and TEM characterization) shows signs of deactivation, with a noticeable drop in conversion over 3 hours TOS. This sample showed high oligomer selectivity (approximately 40-50%). Both 1.5-CP and 1.5-SG samples showed higher ethylene selectivity than the palladium-based Lindlar catalyst and the 10-$SiO_2$ metallic nickel nanoparticle catalyst. In fact, 1.5-SG achieves 100% selectivity when accounting for both ethane and oligomer formation. This is substantially higher selectivity than that found in previously described nickel alloys. (See, e.g., Onda et al., *Phys. Chem. Chem. Phys.* 2000, 2, 2999-3005 (highest ethylene selectivity near 70% with higher order hydrocarbon selectivity ranging from 30-50%) and Spanjers et al., *J. Catal.* 2014, 316, 164-173 (highest selectivity approximately 55%). The remarkable selectivity of the 1.5-SG sample can be attributed to the deposition of oligomers.

CO Oxidation Activity of SG Catalysts

Figure 13:
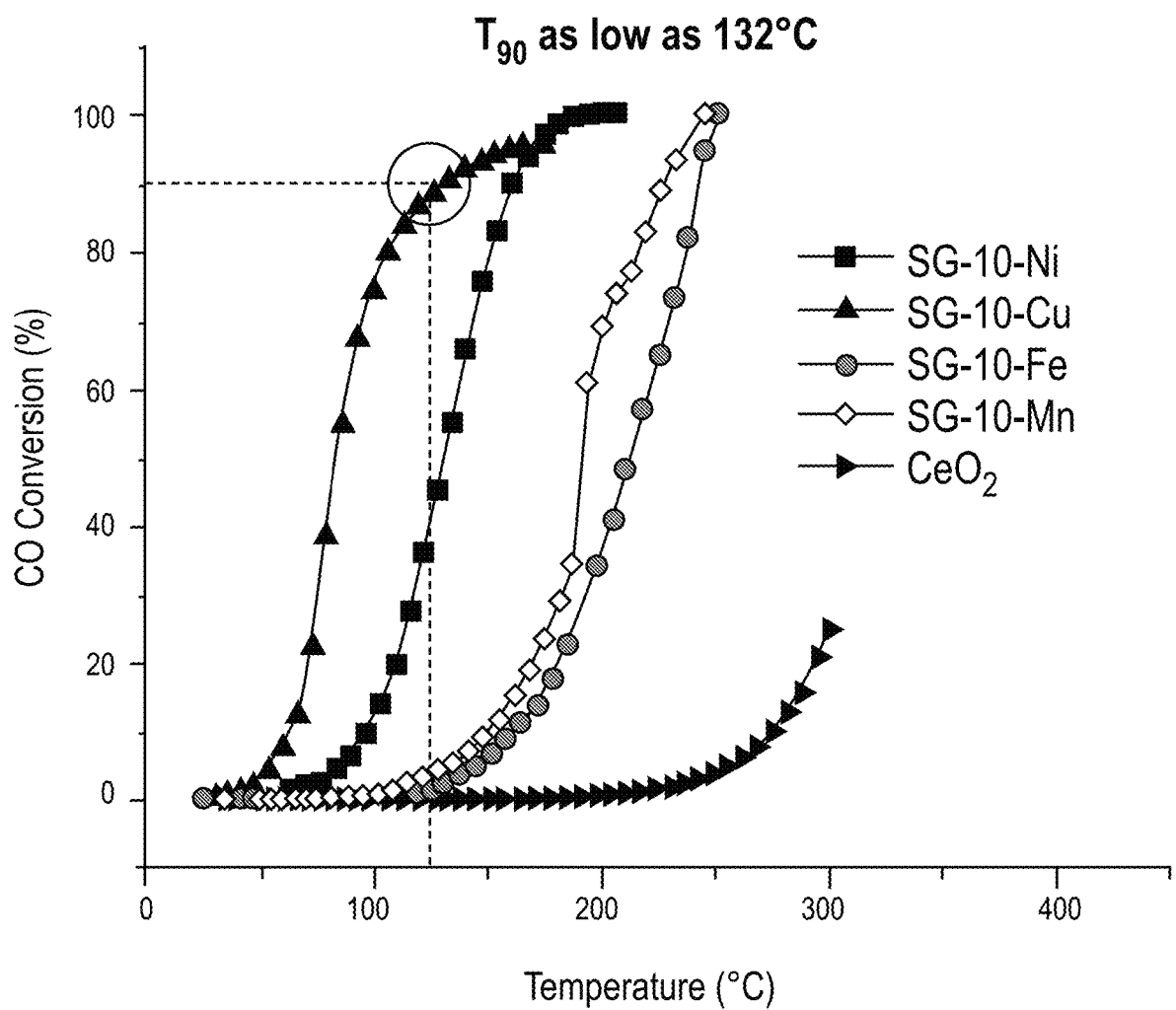
FIG. 13 shows the catalytic activity for CO oxidation of various metal-doped ceria catalysts formed using the SG technique of the present disclosure compared against $CeO_2$.
Figure 14:
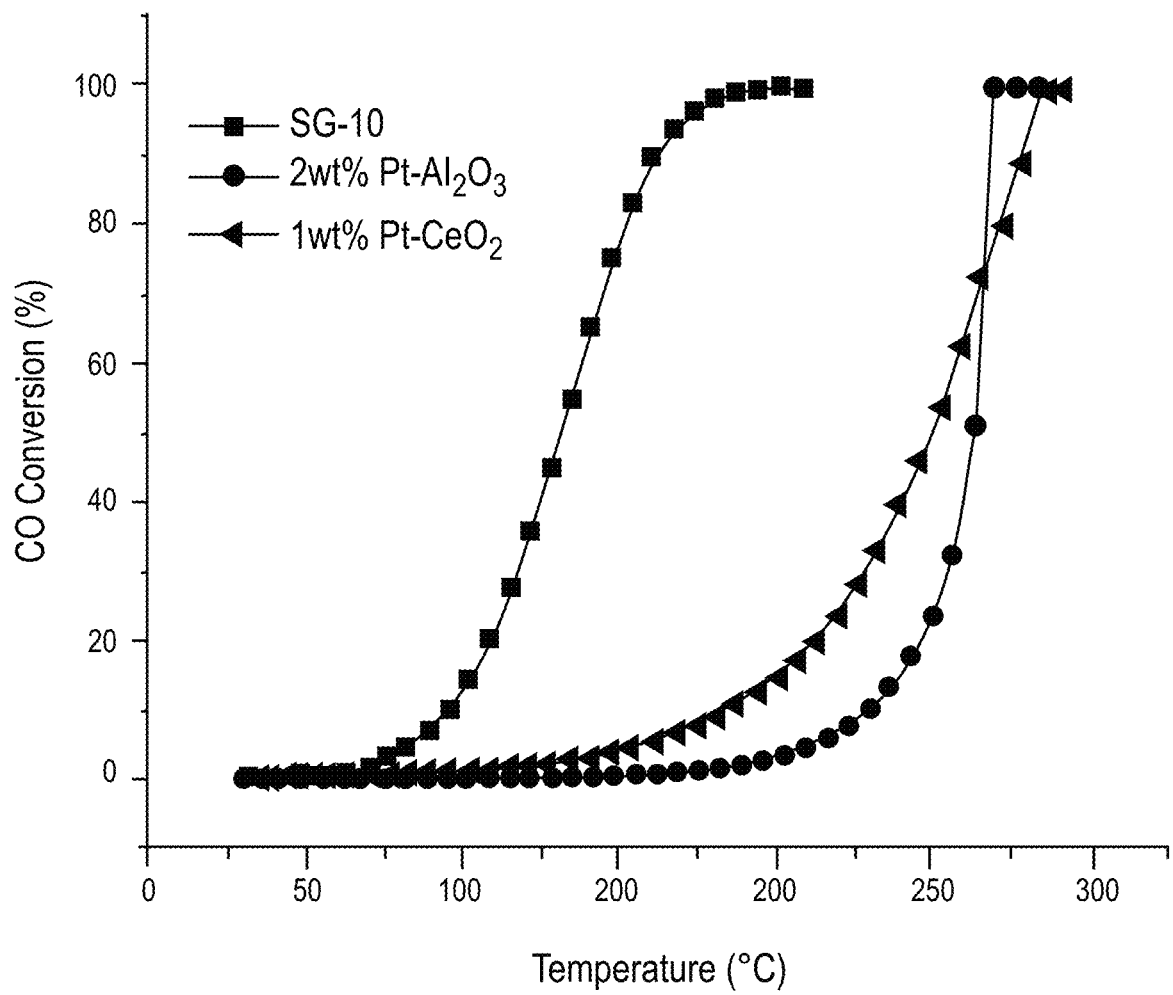
FIG. 14 shows the catalytic activity for CO oxidation of nickel doped ceria formed using the SG technique of the present disclosure compared to conventional platinum catalysts.
Figure 15:
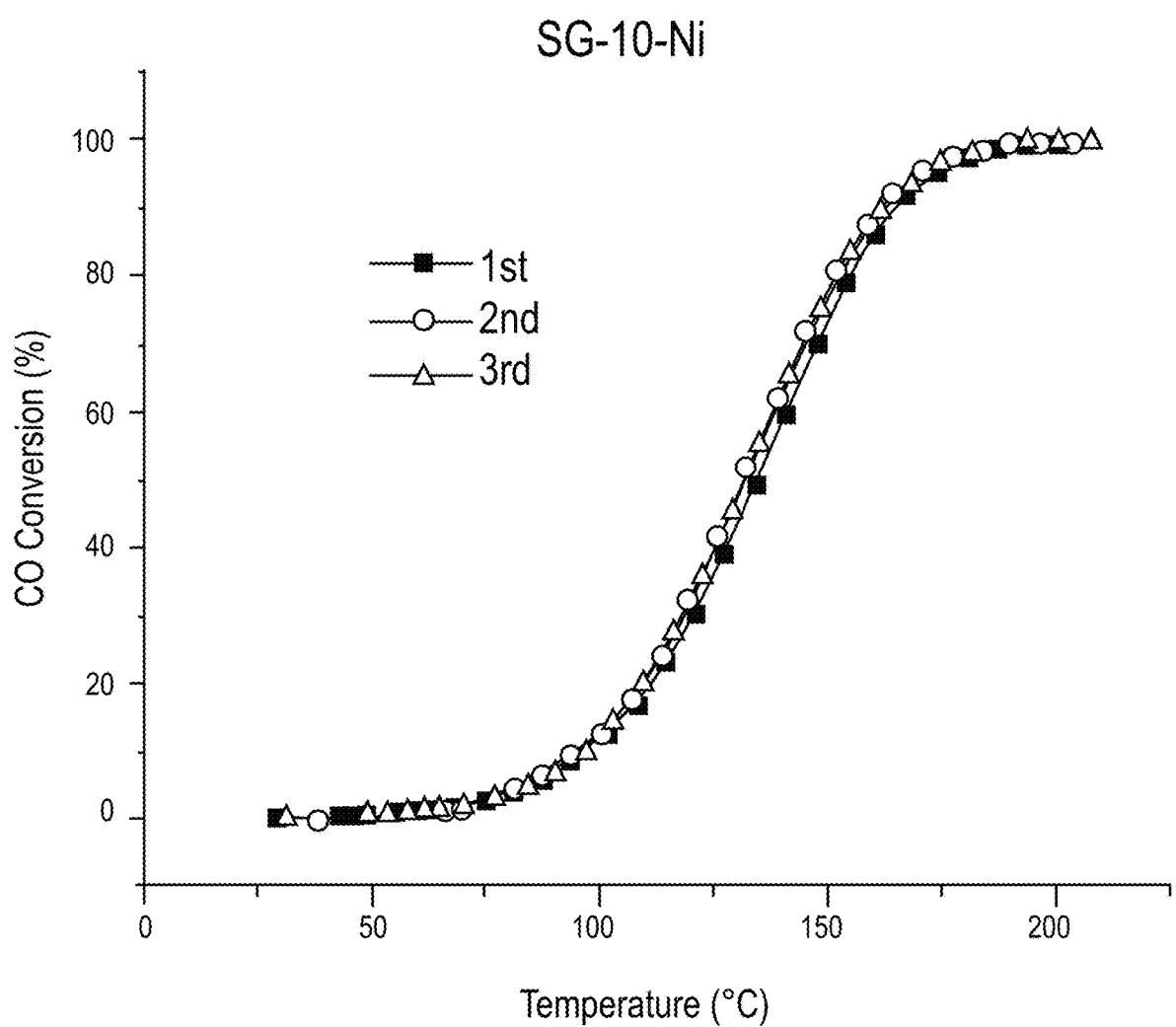
FIG. 15 shows the stability of the SG nickel-ceria catalyst of the present disclosure through repeated use.

The catalytic activity for CO oxidation of various metal-doped ceria catalysts (Nickel, Copper, Iron and Manganese) formed using the SG technique was compared against $CeO_2$ and the results are shown in FIG. 13. The reaction used 20 mg of each catalyst with CO oxidation conditions of 1 ml/min CO, 1.5 ml/min 02, and 75 ml/min He. These results demonstrate that the SG metal-doped ceria catalysts have excellent activity. In fact, as shown in FIG. 14, the SG metal-doped ceria catalyst outperformed conventional Pt catalysts (2 wt % Pt—$Al_2O_3$, 1 wt % Pt-$CeO_2$) without the need for activation. Moreover, as shown in FIG. 15, the SG metal-ceria catalyst remains stable through repeated use.

Figure 16:
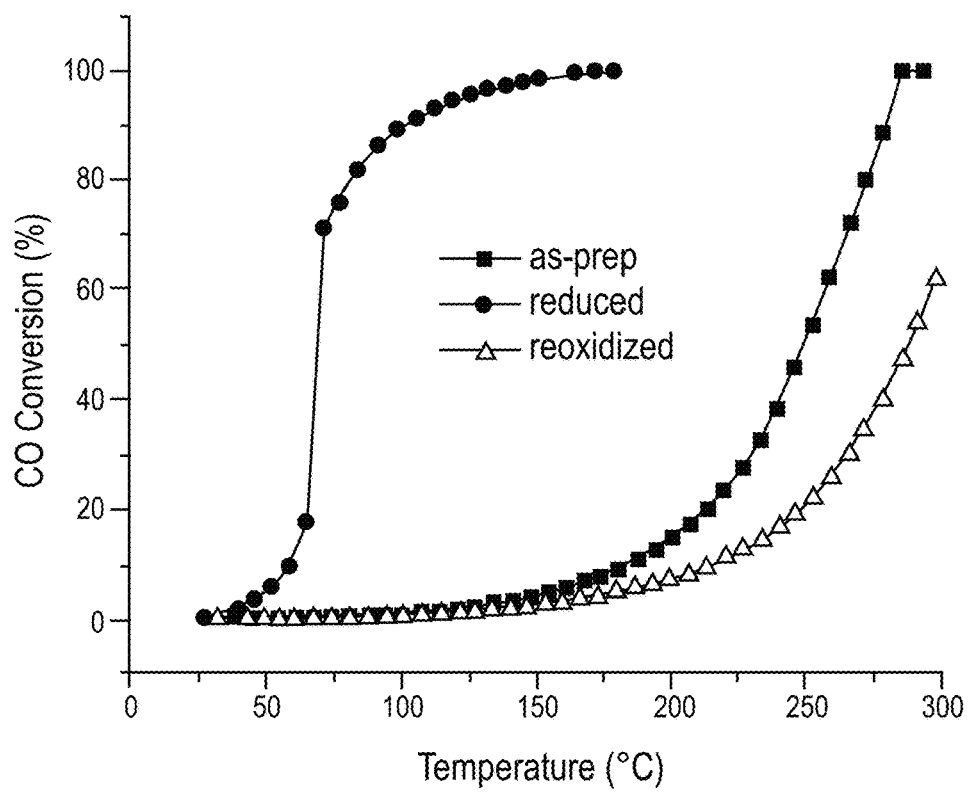
FIG. 16 shows the performance of traditional platinum supported on ceria during and after reduction and reoxidation.
Figure 17:
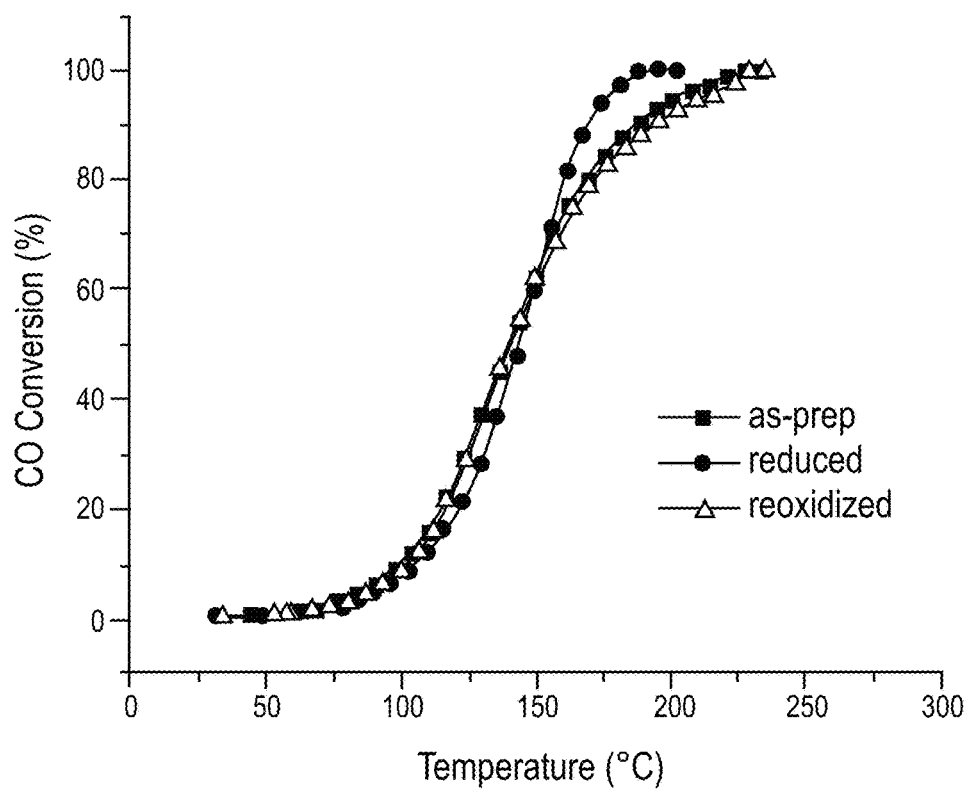
FIG. 17 shows the performance of platinum supported on Ni-doped ceria formed using the SG technique of the present disclosure during and after reduction and reoxidation.
Figure 18:
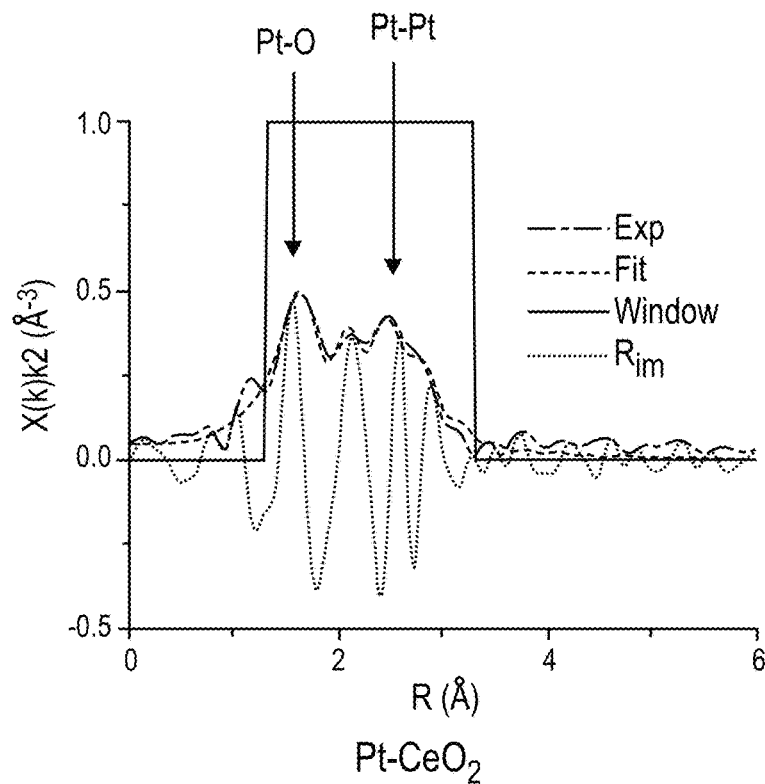
FIG. 18 shows Pt nearest neighbors on traditional ceria-supported platinum catalyst after reduction.
Figure 19:
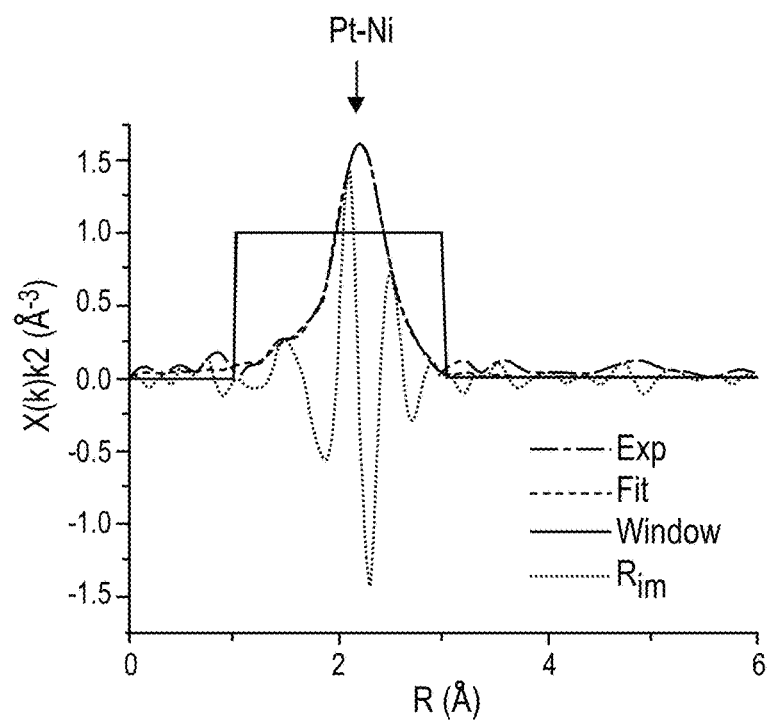
FIG. 19 shows that the Pt nearest neighbors in SG Ni-ceria supported platinum catalyst of the present disclosure after reduction.
Figure 20:
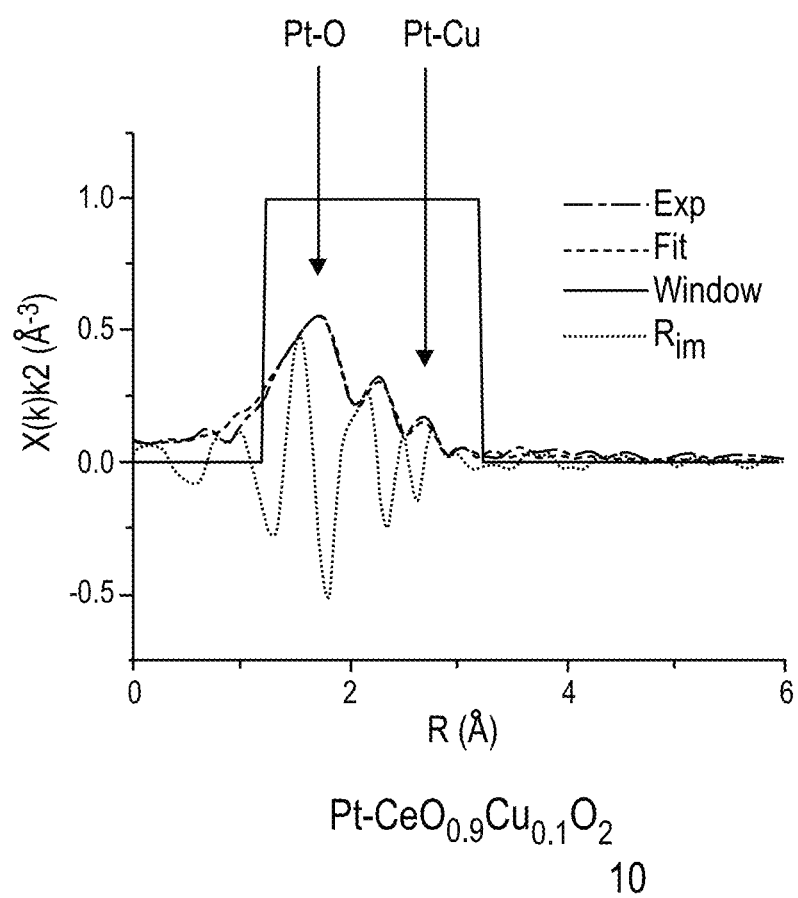
FIG. 20 shows that the Pt nearest neighbors of SG Cu-ceria supported platinum catalyst of the present disclosure after reduction.

Improved Stability of Platinum Supported on Ni-Doped Ceria Formed with SG Technique FIGS. 16 and 17 compare the performance of platinum supported on ceria (FIG. 16) and Ni-doped ceria formed using the SG technique (FIG. 17). As shown, the Pt-$Ce_{0.9}Ni_{0.1}O_2$ material maintained nearly identical levels of CO conversion during both reduction and after reoxidation, while the Pt-$CeO_2$ material performance changes dramatically between reduction and reoxidation. Moreover, as shown in FIGS. 18-20, platinum supported on the SG metal-doped ceria material doesn't sinter into nanoparticles during reduction (FIG. 19 (Pt-$Ce_{0.9}Ni_{0.1}O_2$), 20 (Pt—$Ce_{0.9}Cu_{0.1}O_2$), as opposed to platinum supported on ceria (FIG. 18 (Pt—$CeO_2$). FIGS. 21-24 are images of 1 wt % platinum on standard ceria oxide as-prepared (FIG. 21) and after reduction in CO at 275° C. (FIG. 22) and 1 wt % platinum on the SG $Ce_{0.9}Ni_{0.1}O_{2-\delta}$ material in as prepared (FIG. 23) and after reduction (FIG. 24). These images show that the SG doped ceria supports are able to retain single platinum atoms after exposure to reducing agents, which explains the excellent catalyst stability seen in FIG. 17. On the other hand, platinum supported on conventional undoped ceria sinters to form Pt nanoparticles when exposed to reducing conditions, which is why the catalyst behaves differently under varying conditions as seen in FIG. 16. Compared to previously described catalysts, the ability of the SG materials to retain atomically dispersed platinum under these conditions is unexpected and highly remarkable.

Thermal Stability of Cu-Doped SG Ceria Vs Cu,Al Co-Doped SG Ceria

Figure 25:
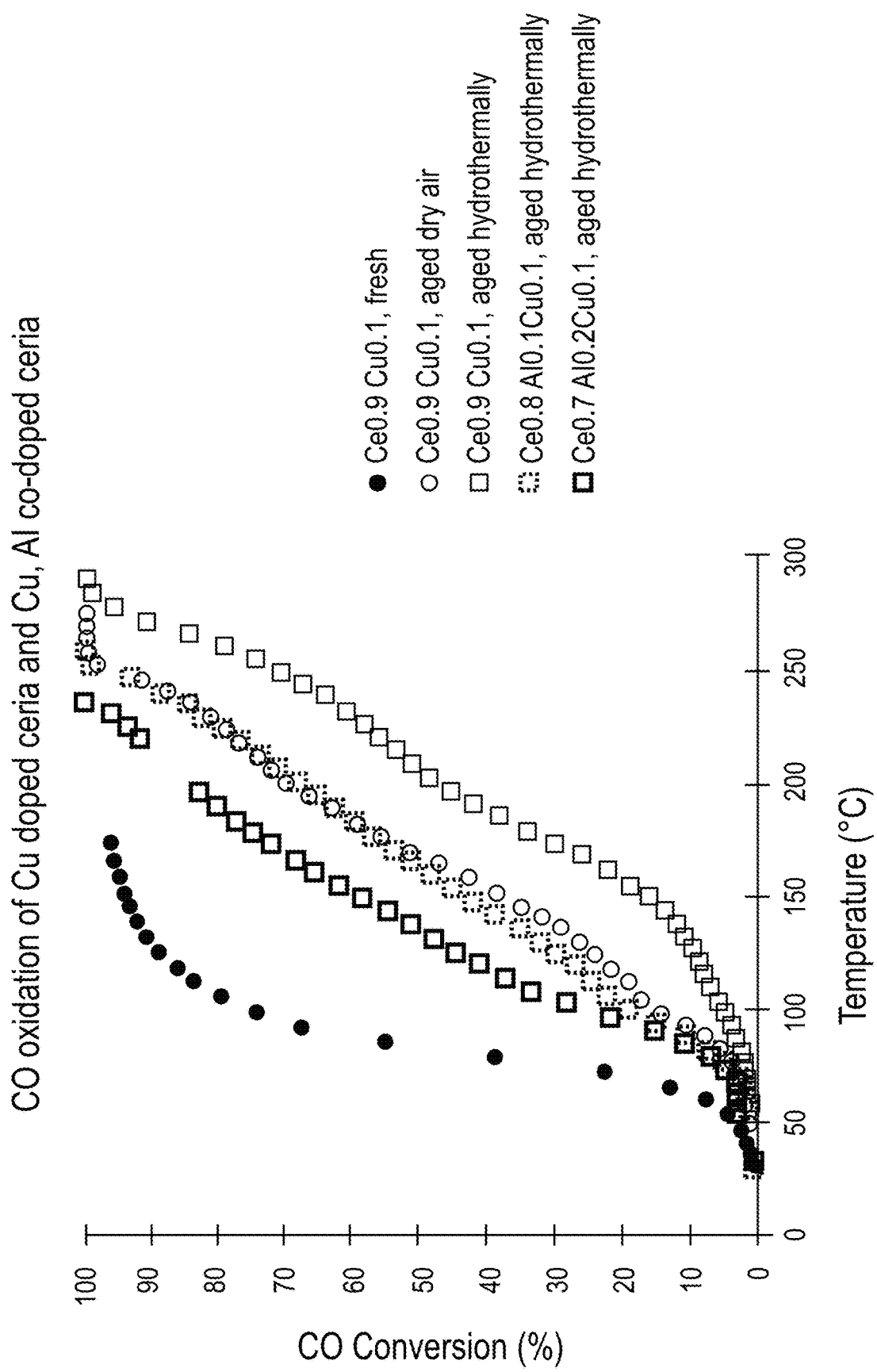
FIG. 25 shows the thermal stability of Cu-doped SG ceria and Cu-doped vs Cu,Al co-doped SG ceria.
Figure 26:
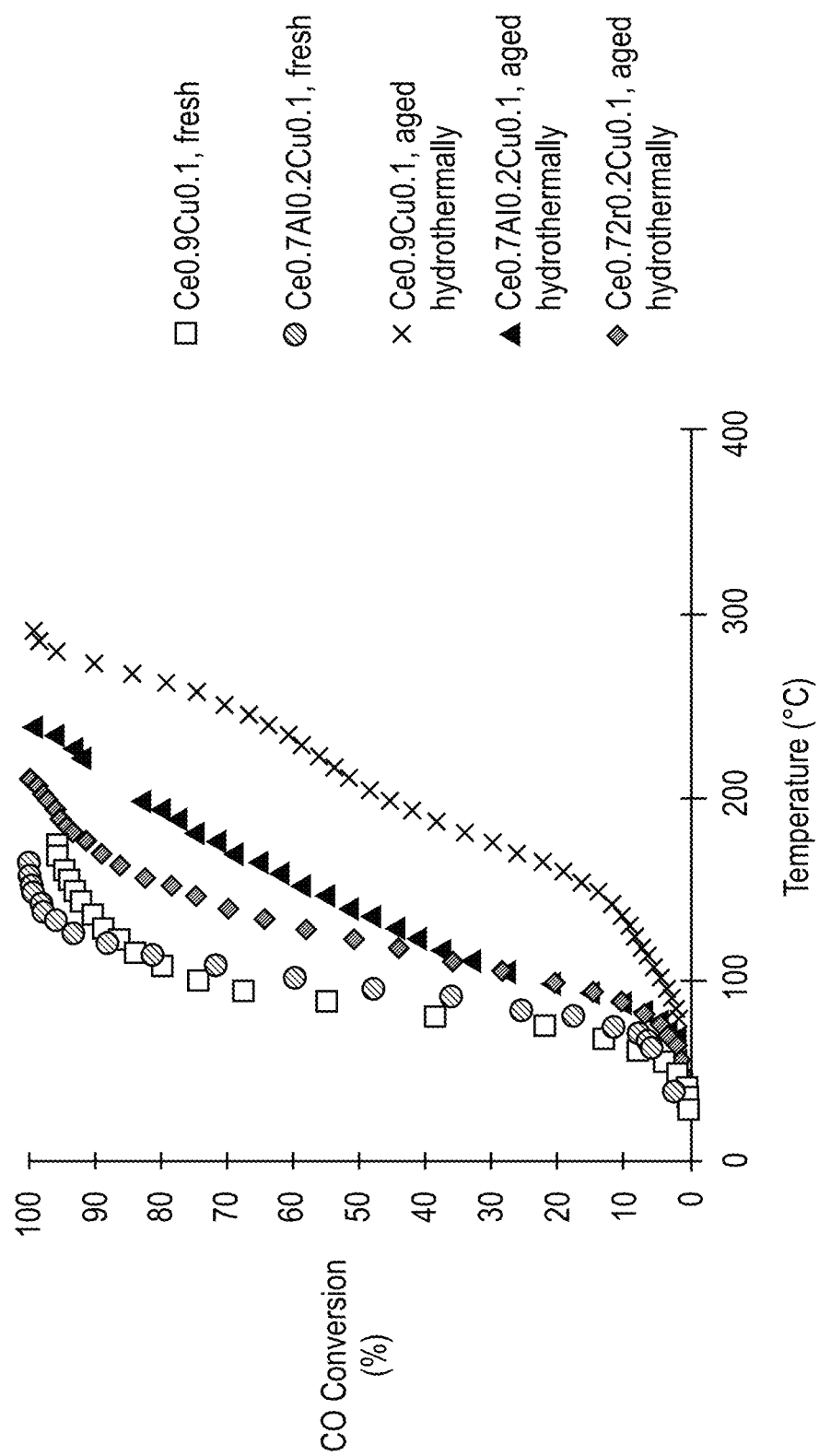
FIG. 26 shows the thermal stability of ZrCu co-doped ceria.

FIG. 25 shows the thermal stability of Cu-doped SG ceria and Cu-doped vs Cu,Al co-doped SG ceria. $Ce_{0.9}Cu_{0.1}O_{2-\delta}$ catalyst (SG-10-Cu) was tested in CO oxidation in fresh and aged states. FIG. 26 includes Zr,Cu co-doped ceria. Aging was conducted in stagnant air within a box furnace at 800° C. for 8 hours and hydrothermally in a tube furnace by flowing air with 10% $H_2O$ concentration at 50 ml/min at 800° C. for 8 hours, 10° C./min ramp rate in both aging protocols. As shown, Cu-doped ceria deactivates significantly in both aging conditions. However, the addition of aluminum or zirconium dopants provides hydrothermal stability. The specific surface areas of the as-prepared and hydrothermally aged materials are shown in Table 5.

TABLE 5

| Sample | Specific Area, as prepared ($m^2/g$) | Specific surface area, hydrothermally aged ($m^2/g$) |
| --- | --- | --- |
| $Ce_{0.9}Cu_{0.1}O_{2-\delta}$ | 179 | 4.4 |
| $Ce_{0.8}Al_{0.1}Cu_{0.1}O_{2-\delta}$ | 179 | 5.1 |
| $Ce_{0.7}Al_{0.2}Cu_{0.1}O_{2-\delta}$ | 177 | 10.4 |
| $Ce_{0.7}Zr_{0.2}Cu_{0.1}O_{2-\delta}$ | 145 | 10.5 |

Stable Reactivity of Ni-Doped SG Ceria for Dry Reforming

Figure 27:
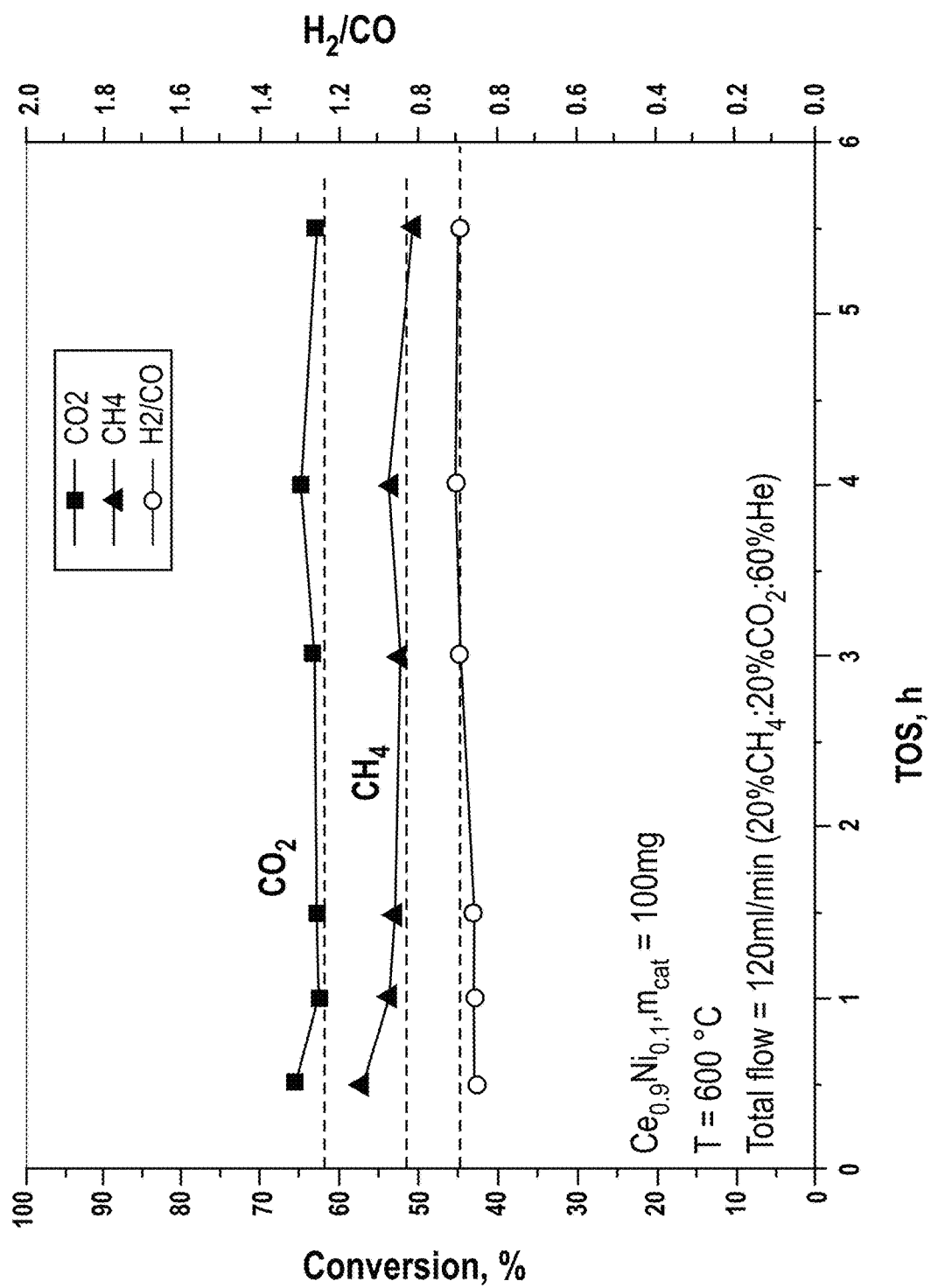
FIG. 27 demonstrates the stable performance of Ni-doped SG ceria for methane dry reforming.

As shown in FIG. 27, Ni-doped SG ceria is not as prone to deactivation due to coke formation as conventional nickel-based methane dry reforming catalysts. Once again, this demonstrates that the Ni in the SG sample is very different from that in conventional Ni based catalysts.

Synthesis of SG $MgAl_2O_4$ Spinel

Figure 28:
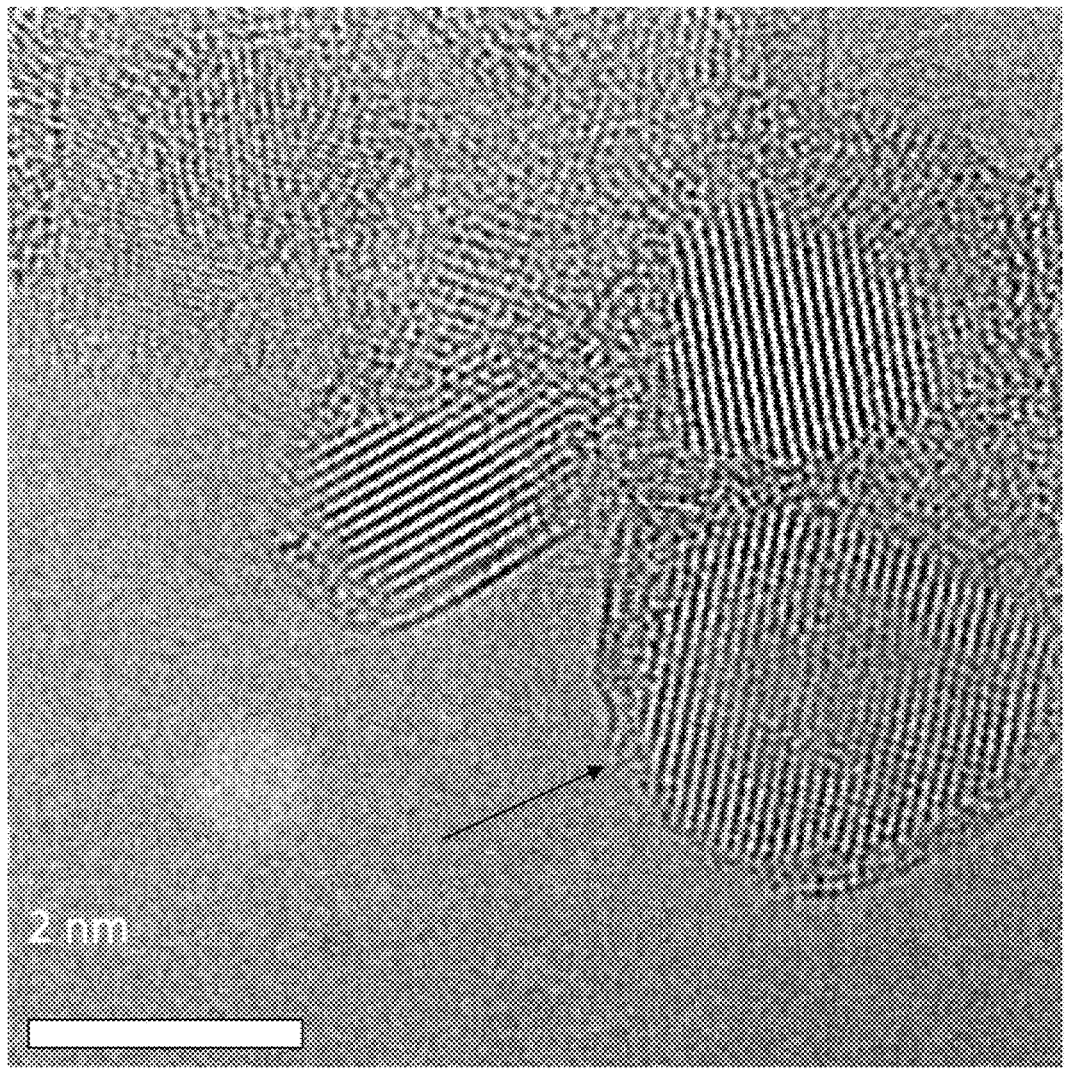
FIG. 28 is an image of commercially available $MgAl_2O_4$ spinel.
Figure 29:
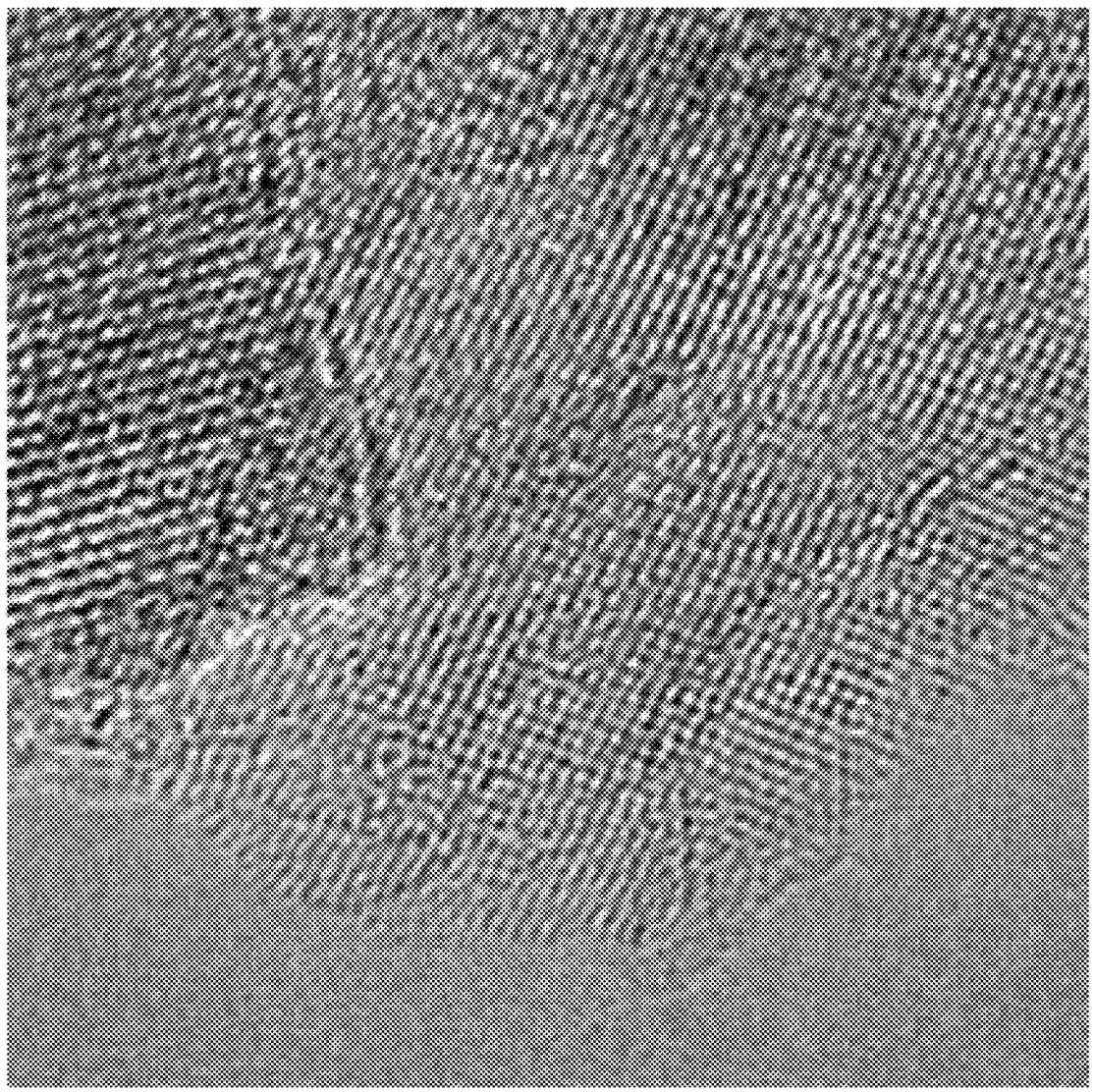
FIG. 29 is an image of SG $MgAl_2O_4$ spinel of the present disclosure.

FIGS. 28 and 29 are comparative images of commercially available $MgAl_2O_4$ spinel (FIG. 28) and SG $MgAl_2O_4$ spinel (FIG. 29). As shown, the SG $MgAl_2O_4$ formed using the presently described SG technique does not have the amorphous layers (arrow, FIG. 28) that is clearly present in the commercially available material. The amorphous layers are a result of deviation from stoichiometry. The SG technique allows tight control of the ratio of the metal components at the nanoscale.

What is claimed is:

1. A metal-doped oxide material having a surface area greater than 120 $m^2/g$, wherein the material comprises a metal and a cerium oxide lattice, wherein the metal is homogeneously dispersed in the form of isolated metal ions uniformly distributed throughout the cerium oxide lattice.

2. The metal-doped oxide material of claim 1 wherein, the metal is a transition metal, post-transition metal, alkaline-earth metal, or lanthanide metal.

3. The metal-doped oxide material of claim 1, wherein the material is doped with more than one metal.

4. The metal-doped oxide material of claim 1, wherein the metal is selected from the group consisting of nickel, platinum, copper, iron, manganese, aluminum, zirconium and combinations or alloys thereof.

5. The metal-doped oxide of claim 1 is formed by:
dissolving a polymer in a solvent to produce a polymer solution;
adding a metal nitrate and cerium nitrate to the polymer solution to produce a metal-cerium solution;
allowing the metal-cerium solution to form a hard gel;
forming a powder from the gel; and
calcining the powder.

6. The metal of claim 5, wherein the polymer is selected from the group consisting of polyvinylpyrrolidone (PVP), polyethylene glycol (PEG), and hydroxypropyl cellulose (HPC).

7. The metal of claim 5, wherein the polymer is polyvinylpyrrolidone (PVP).

8. The metal of claim 5, wherein the metal is selected from the group consisting of nickel, platinum, copper, iron, manganese, aluminum, zirconium and combinations or alloys thereof.

9. The metal-doped oxide material of claim 1, wherein the metal is atomically dispersed within the cerium oxide lattice and does not form any separate crystalline phase.

10. A catalytic converter comprising the metal-doped oxide material of claim 1.

11. A hydrogenation catalyst comprising the metal-doped oxide material of claim 1.

12. An oxygen transfer catalyst comprising the metal-doped oxide material of claim 1.

13. A catalyst comprising the metal-doped oxide material of claim 1.

14. The catalyst of claim 13, wherein the catalytic material is platinum.

* * * * *